US010829827B2

(12) United States Patent
Tilloy et al.

(10) Patent No.: US 10,829,827 B2
(45) Date of Patent: Nov. 10, 2020

(54) METHOD FOR OBTAINING LOW ETHANOL-PRODUCING YEAST STRAINS, YEAST STRAINS OBTAINED THEREFROM AND THEIR USE

(71) Applicants: Danstar Ferment AG, Zug (CH); Institut National De La Recherche Agronomique (INRA), Paris (FR)

(72) Inventors: Valentin Tilloy, Le Chesnay (FR); Anne Ortiz-Julien, Gagnac sur Garonne (FR); Jessica Noble, Lattes (FR); Sylvie Dequin, Montpellier (FR)

(73) Assignees: DANSTAR FERMENT AG, Zug (CH); INSTITUT NATIONAL DE RECHERCHE POUR L'AGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 0 days.

(21) Appl. No.: 15/115,151

(22) PCT Filed: Jan. 30, 2015

(86) PCT No.: PCT/EP2015/051995
§ 371 (c)(1),
(2) Date: Jul. 28, 2016

(87) PCT Pub. No.: WO2015/114115
PCT Pub. Date: Aug. 6, 2015

(65) Prior Publication Data
US 2016/0348192 A1 Dec. 1, 2016

(30) Foreign Application Priority Data
Jan. 31, 2014 (EP) .................................... 14290019

(51) Int. Cl.
| | |
|---|---|
| C12N 1/36 | (2006.01) |
| C12N 1/16 | (2006.01) |
| C12G 1/022 | (2006.01) |
| C12P 7/20 | (2006.01) |
| C12R 1/865 | (2006.01) |
| C12P 7/06 | (2006.01) |

(52) U.S. Cl.
CPC ............ *C12R 1/865* (2013.01); *C12G 1/0203* (2013.01); *C12N 1/16* (2013.01); *C12N 1/36* (2013.01); *C12P 7/06* (2013.01); *C12P 7/20* (2013.01); *C12G 2200/05* (2013.01); *Y02E 50/17* (2013.01)

(58) Field of Classification Search
None
See application file for complete search history.

(56) References Cited

PUBLICATIONS

Eglinton et al., Decreasing acetic acid accumulation by a glycerol overproducing strain of *Saccharomyces cerevisiae* by deleting the ALD6 aldehyde dehydrogenase gene, Yeast 2002; vol. 19, pp. 295-301.*
Aguera et al., "Pilot Scale Vinifications (100 L) I: The Controlled Fermentations Facility at the Inra in Pech Rouge," *Wine Internet Technical Journal* #4, 2005. (8 pages).
Bely et al., "Automatic Detection of Assimilable Nitrogen Deficiencies during Alcoholic Fermentation in Oenological Conditions," *Journal of Fermentation and Bioengineering* 70(4):246-252, 1990.
Blomberg et al., "Physiology of Osmotolerance in Fungi," in Rose (ed.), *Advances in Microbial Physiology* 33, Academic Press Limited, London, United Kingdom, 1992, pp. 146-212. (71 pages).
Cambon et al., "Effects of GPD1 Overexpression in *Saccharomyces cerevisiae* Commercial Wine Yeast Strains Lacking ALD6 Genes," *Applied and Environmental Microbiology* 72(7):4688-4694, 2006.
Hagenauer-Hener et al., "Butane-2,3 diol—Directly Determination of the Stereoisomers in Wine," *Deutsche Lebensmittel-Rundschau* 9:273-276, 1990. (7 pages) (with Partial English Machine Translation).
Kutyna, "Isolation of Low Ethanol Producing Yeast Strains Using Adaptive Evolution," doctoral dissertation, Victoria University, Melbourne, Australia, 2008, 42 pages.
Kutyna et al., "Adaptive evolution of *Saccharomyces cerevisiae* to generate strains with enhanced glycerol production," *Applied Microbiology and Biotechnology* 93(3):1175-1184, 2012.
Kutyna et al., "Microbiological approaches to lowering ethanol concentration in wine," *Trends in Food Science & Technology* 21(6):293-302, 2010.
Lundquist, "Determination with Aldehyde Dehydrogenase," in Bergmeyer (ed.), *Methods of Enzymatic Analysis*: vol. 3, Academic Press, London, United Kingdom, 1974, pp. 1509-1513. (6 pages).
Michnick et al., "Modulation of Glycerol and Ethanol Yields During Alcoholic Fermentation in *Saccharomyces cerevisiae* Strains Overexpressed or Disrupted for GPD1 Encoding Glycerol 3-Phosphate Dehydrogenase," *Yeast* 13(9):783-793, 1997.

(Continued)

*Primary Examiner* — Michelle F. Paguio Frising
(74) *Attorney, Agent, or Firm* — Seed IP Law Group LLP

(57) ABSTRACT

The present disclosure concerns a process for obtaining a variant yeast strain capable of producing less ethanol in an alcoholic fermentation process than its corresponding ancestral strain. The variant yeast strain is obtained by culturing the ancestral strain in the presence of increasing concentrations of a salt capable of causing an hyperosmotic stress to the ancestral yeast strain. The present disclosure also concerns variant yeast strain obtained from this process (for example the variant yeast strain deposited at Institut Pasteur, on Jan. 9, 2014, under accession number CNCM I-4832, the variant yeast strain deposited at Institut Pasteur, on Oct. 18, 2012 under accession number CNCM I-4684, the variant yeast strain deposited at Institut Pasteur, on Oct. 18, 2012 under accession number CNCM I-4685 and/or the variant yeast strain deposited at Institut Pasteur on Jan. 28, 2015 under accession number CNCM I-4952) as well as processes using the variant yeast strain (wine fermentation for example).

19 Claims, 7 Drawing Sheets

Specification includes a Sequence Listing.

(56) References Cited

PUBLICATIONS

Petrovska et al., "Glycerol production by yeasts under osmotic and sulfite stress," *Canadian Journal of Microbiology* 45(8):695-699, 1999.

Remize et al., "Glycerol Overproduction by Engineered *Saccharomyces cerevisiae* Wine Yeast Strains Leads to Substantial Changes in By-Product Formation and to a Stimulation of Fermentation Rate in Stationary Phase," *Applied and Environmental Microbiology* 65(1): 143-149, 1999.

Casey et al., "Effect of salts on the Co-fermentation of glucose and xylose by a genetically engineered strain of *Saccharomyces cerevisiae*," *Biotechnology for Biofuels* 6:83, 2013, 10 pages.

Omori et al., "Breeding of High Glycerol-Producing *Shochu* Yeast (*Saccharomyces cerevisiae*) with Acquired Salt Tolerance," *Journal of Fermentation and Bioengineering* 79(6):560-565, 1995.

\* cited by examiner

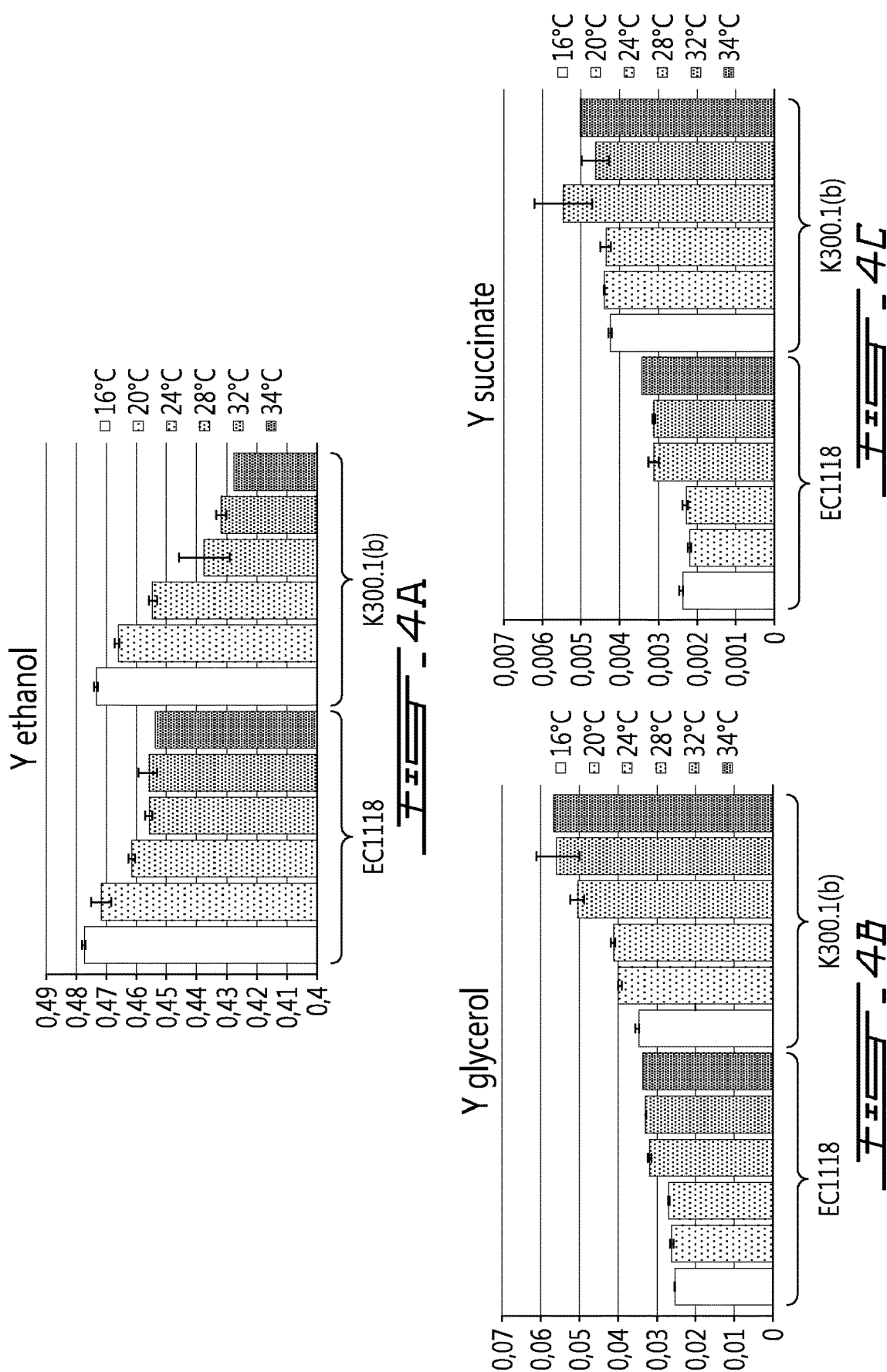

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Oligonucleotide used to distinguish between
      MATa and MATalpha genes

<400> SEQUENCE: 1
agtcacatca agatcgttta tgg                                              23

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide used to distinguish between
      MATa and MATalpha genes

<400> SEQUENCE: 2
actccacttc aagtaagagt ttg                                              23

<210> SEQ ID NO 3
<211> LENGTH: 23
<212> TYPE: DNA
<213> ORGANISM: Artificial Sequence
<220> FEATURE:
```

```
<223> OTHER INFORMATION: Oligonucleotide used to distinguish between
      MATa and MATalpha genes

<400> SEQUENCE: 3
gcacggaata tgggactact tcg                                              23
```

METHOD FOR OBTAINING LOW ETHANOL-PRODUCING YEAST STRAINS, YEAST STRAINS OBTAINED THEREFROM AND THEIR USE

CROSS-REFERENCE TO RELATED APPLICATIONS AND DOCUMENTS

This application claims priority from EP patent application serial number 14290019.0 filed on Jan. 31, 2014. This application also includes a sequence listing (entitled "Sequencelisting" and having 4 kb). This application further includes the following biological deposits (all made at Institut Pasteur) under accession number Collection Nationale des Cultures des Microorganismes (CNCM) I-4832 (deposited on Jan. 9, 2014), CNCM I-4684 (deposited on Oct. 18, 2012), CNCM I-4685 (deposited on Oct. 18, 2012) and CNCM I-4952 (deposited on Jan. 28, 2015).

The content of the priority application, the biological deposits and the sequence listing is herewith incorporated in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 240141_401USPC_SEQUENCE_LISTING.txt. The text file is 1 KB, was created on Jul. 13, 2016, and is being submitted electronically via EFS-Web.

TECHNOLOGICAL FIELD

The present disclosure relates to a process for obtaining non-genetically-modified variant yeast strains which have the ability of producing less ethanol than their corresponding ancestral/parental strains as well as variant yeast strains obtained or derived from this process. The present disclosure also relates the use of such variant yeast strain during an alcoholic fermentation process, such as the production of wine.

BACKGROUND

Over the past twenty years, the alcohol content of wine has increased considerably, by about 2% (v/v), as a result of the high sugar content of the grapes currently used. This is mainly due to developments in winemaking practices, with the harvest of very mature grapes being favored to adapt to consumer demand for rich and ripe fruit flavor in wine. This trend poses major problems for the wine industry. The market is currently oriented towards beverages with moderate alcohol contents, in line with public prevention policies, consumer health issues and preferences. In addition, as some countries impose taxes on the alcohol content, this trend raises economic issues. High levels of alcohol can alter the sensorial quality of wines, by increasing the perception of hotness and, to a lesser extent, by decreasing the perception of sweetness, acidity and aroma. Also, high ethanol levels generated during fermentation may inhibit yeast activity and can lead to sluggish or stuck fermentations. Consequently, reducing the ethanol content of wine has been a major focus of wine research, at various steps of the winemaking process. Several viticulture strategies are being developed to decrease sugar accumulation on grapes. These approaches include the selection of adequate grape varieties that accumulate less sugar and the modification of culture techniques to reduce the berry sugar accumulation, such as irrigation, canopy management or limitation of photosynthesis. Physical techniques for de-alcoholisation, for example reverse osmosis, nano-filtration or distillation have also been developed and are available in the short-term. However, de-alcoholisation treatments are expensive to implement, and may have detrimental effects on the organoleptic quality of the wine.

An attractive and inexpensive option would be to use yeasts that produce less alcohol from the same amount of sugar. Indeed, there have been many efforts to develop engineered wine yeast strains with reduced ethanol yield. One of the most efficient approaches was to divert metabolism towards increased production of glycerol and thus away from ethanol. In *Saccharomyces cerevisiae*, glycerol plays major roles in redox homeostasis and in osmotic stress resistance: it is the main compatible solute in yeast. Glycerol is usually found in wines at concentrations in the range 5 to 9 g/L and contributes positively to the quality of wine by providing body and sweetness. It may also confer viscosity at very high concentrations (above 25 g/L), as in *Botrytis* wines. Rerouting carbon towards glycerol led to a substantial decrease in ethanol production and accumulation of various compounds, including acetate and acetoin, both undesirable for wine sensorial quality. Rational engineering of key reactions at the acetaldehyde branch point allowed the accumulation of these undesirable compounds to be limited. This resulted in low alcohol strains being obtained in which the carbon flux was redirected towards glycerol and 2,3-butanediol, a polyol with no sensorial impact in wines. These engineered wine yeasts have the potential to reduce the alcohol content of wine by 1 to 3% (v/v). However, the poor consumer acceptance of DNA recombinant technology in food is a major barrier to their commercialization. Consequently, there is a great interest to use alternative, non-genetically modified organism (GMO) approaches to improve the properties of wine yeast strains.

It would be highly desirable to be provided with non-genetically modified variants yeast strains capable of producing less ethanol than their corresponding ancestral yeast strains. Preferably, the alcoholic fermentation of these variant yeast strain does not lead to the production of undesirable organoleptic properties in the fermented product.

BRIEF SUMMARY

The present disclosure provides a process for obtaining a variant yeast strain capable of producing, when compared to an ancestral yeast strain, more glycerol and less ethanol during an alcoholic fermentation process. The process relies on the use of a salt capable of causing an hyperosmotic stress to the ancestral yeast strain as well as culturing the yeast strain in a high concentration of a carbon source until exhaustion of the carbon source. Surprisingly, the variant yeast strain obtained produce more glycerol and less ethanol than the ancestral yeast strain from which they are derived, even in the absence of the salt. In an embodiment, the variant yeast strain is not more resistant to the hyperosmotic stress than its corresponding ancestral yeast strain, but displays increased viability and a gain of fitness in carbon starvation conditions when compared to its ancestral yeast strain. In some embodiments, the variant yeast strain (when compared to the ancestral yeast strain) produces the same amount or less of acetate and/or acetoin during an alcoholic fermentation.

According to a first aspect, the present disclosure provides a process for obtaining a variant yeast strain capable of producing, when compared to an ancestral yeast strain, more glycerol and less ethanol in an alcoholic fermentation process. Broadly, the process comprises a) culturing the ancestral yeast strain in a first culture medium comprising a salt capable of causing an hyperosmotic stress to the ancestral yeast strain, wherein the ancestral yeast strain is cultured in increasing salt concentrations and under conditions to achieve glucose depletion in the first culture medium so as to obtain a first cultured yeast strain; and b) culturing the first cultured yeast strain in a second culture medium comprising the salt, wherein the first cultured yeast strain is cultured at a fixed salt concentration and under conditions to achieve glucose depletion in the second culture medium so as to obtain the variant yeast strain. The salt used in the process has a countercation which is different than a sodium cation. In the process, the concentration of the salt in the second culture medium is higher than the concentration of the salt in the first culture medium. In an embodiment, the concentration of the salt in the first culture medium is between about 1.25 M and less than about 1.9 M or about 2.4 M. In another embodiment, the concentration of the salt in the second culture medium is at least about 2.4 M. In an embodiment, the process further comprises, at step a), increasing the salt concentration weekly or monthly. In still another embodiment, the first culture medium comprises glucose and the process further comprises, at step a), culturing the ancestral yeast strain in the first culture medium while decreasing glucose concentrations. In such embodiment, the concentration of glucose can be decreased weekly or monthly. Further, still in such embodiment, the concentration of glucose in the first culture medium can be between about 14.0% and about 8.0% (w/v) or between about 14.0% and about 9.6% (w/v) with respect to the total volume of the first culture medium. In another embodiment, the second culture medium comprises glucose and the process further comprises, at step b), culturing the first cultured yeast at a fixed glucose concentration. In such embodiment, the fixed glucose concentration of the second culture medium is preferably 8.0% (w/v) with respect to the total volume of the second culture medium. In an embodiment, the process can further comprise mating haploid spores of the variant yeast strain to obtain a variant hybrid strain. In still another embodiment, the salt has a potassium cation, such as, for example, KCl. In yet another embodiment, the ancestral and/or variant yeast strain is from a *Saccharomyces* species and preferably from a genus selected from the group consisting of *Saccharomyces arboricolus, Saccharomyces eubayanus, Saccharomyces bayanus, Saccharomyces cerevisiae, Saccharomyces kudriadzevii, Saccharomyces mikatae, Saccharomyces paradoxus, Saccharomyces pastorianus, Saccharomyces carsbergensis, Saccharomyces uvarum* and inter-species hybrids.

According to a second aspect, the present disclosure provides a variant yeast strain capable of producing, when compared to an ancestral yeast strain, more glycerol and less ethanol in an alcoholic fermentation process. In an embodiment, the variant yeast is obtained by the process described herein. In an embodiment, the variant yeast strain obtained can be used for making a fermented product, such as wine (e.g., red wine) or beer. In an embodiment, the variant yeast strain is at least one of the one deposited at Institut Pasteur, on Jan. 9, 2014, under accession number Collection Nationale des Cultures des Microorganismes (CNCM) I-4832, the one deposited at Institut Pasteur, on Oct. 18, 2012 under accession number Collection Nationale des Cultures des Microorganismes (CNCM) I-4684 and the one deposited at Institut Pasteur, on Oct. 18, 2012 under accession number Collection Nationale des Cultures des Microorganismes (CNCM) I-4685, on Jan. 28, 2015 under accession number Collection Nationale des Cultures des Microorganismes (CNCM) I-4952 as well as any combination thereof.

According to a third aspect, the present disclosure provides a process for making a fermented product. Broadly, the process comprises contacting the variant yeast strain described herein with a fermentable source of nutrients. In an embodiment, the fermented product is wine (e.g., red wine) and the fermentable source of nutrients is a grape must. In another embodiment, the fermented product is beer and the fermentable source of nutrient is starch (e.g., derived from cereals such as barley for example).

BRIEF DESCRIPTION OF THE DRAWINGS

Having thus generally described the nature of the invention, reference will now be made to the accompanying drawings, showing by way of illustration, a preferred embodiment thereof, and in which:

FIG. 4 shows by-product yields for strains EC1118 and K300.1(b). Metabolites were measured after 30 days of fermentation in 300 mL of MS210, 260 g/L glucose at 16° C., 20° C., 24° C., 28° C., 32° C. and 34° C. Results are shown for ethanol (A, provided as g/g of consumed glucose in function of time and of strain used), glycerol (B, provided as g/g of consumed glucose in function of time and strain used) and succinate (C, provided as g/g of consumed glucose in function of time and strain used). Each points includes the measured valued as well as the standard deviation.

DETAILED DESCRIPTION

Figure 1A:
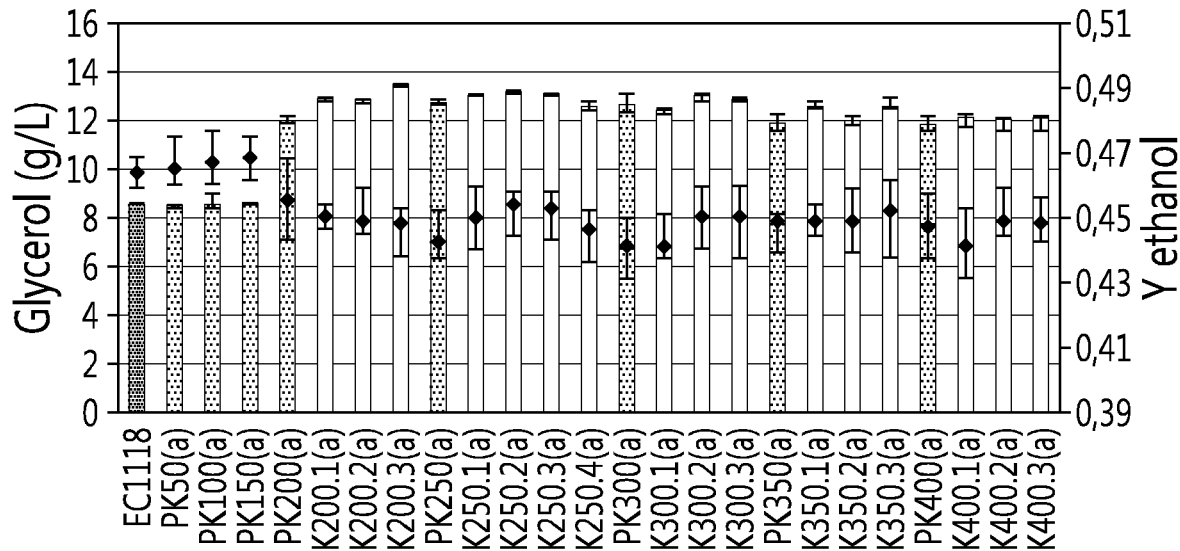
FIG. 1 shows glycerol concentration (bars providing the minimal and maximal concentration) and ethanol yield (black lozenges with the error bars providing minimal and maximal yields) (A, B), and glycerol concentration (bars) and residual glucose after 15 (white triangles with the error bars providing maximal and minimal concentrations) and 30 (black triangles with the error bars providing maximal and minimal concentrations) days of fermentation (C, D) for the ancestral strain (EC1118), evolved populations (dark grey, label starting with "PK") and isolates (evolved strains) (light grey, label starting with "K") from the independent lineages a (A, C) and b (B, D). Fermentations were carried out in 300 mL MS210, 260 g/L glucose, at 28° C. in triplicate. The number in the different labels refers to the number of generations that the populations and strains were submitted to adaptive evolution.
Figure 1B:
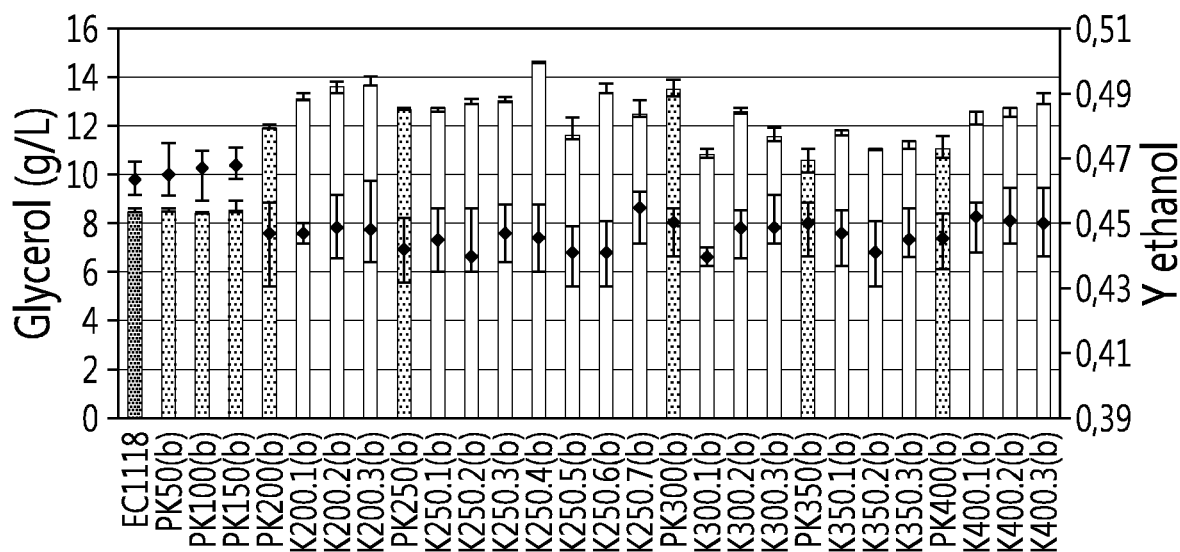
Figure 1C:
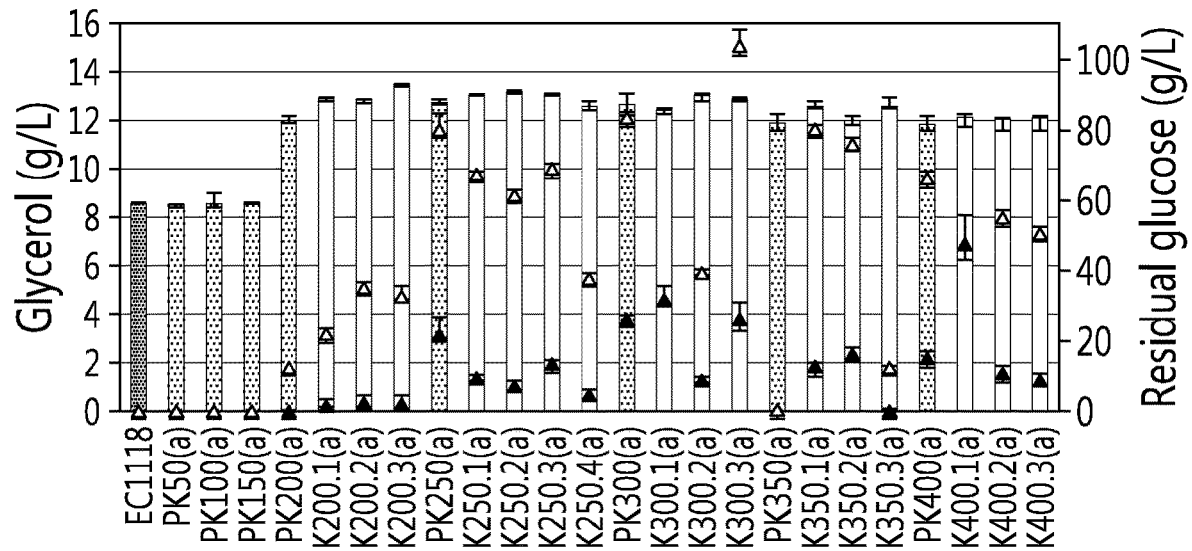
Figure 1D:
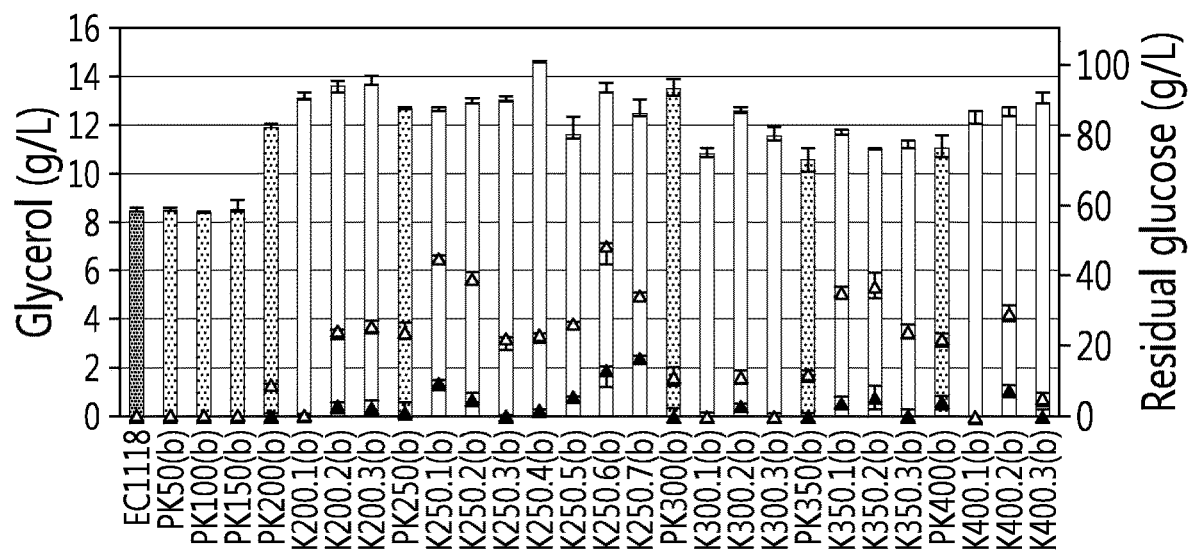

An attractive and inexpensive option to obtain wine having a lower alcohol content would be to use yeasts that produce less alcohol from the same amount of sugar. Indeed, there have been many efforts to develop engineered wine yeast strains with reduced ethanol yield. One of the most efficient approaches was to divert metabolism towards increased production of glycerol and thus away from ethanol. In *Saccharomyces cerevisiae*, glycerol plays major roles in redox homeostasis and in osmotic stress resistance: it is the main compatible solute in yeast. Glycerol is usually found in wines at concentrations in the range 5 to 9 g/L and contributes positively to the quality of wine by providing body and sweetness. It may also confer viscosity at very high concentrations (above 25 g/L), as in *Botrytis* wines. Usually, rerouting carbon towards glycerol led to a substantial decrease in ethanol production and accumulation of various compounds, including acetate and acetoin, both undesirable for wine sensorial quality. Rational genetic engineering of key reactions at the acetaldehyde branch point allowed the accumulation of these undesirable compounds to be limited. This resulted in low alcohol strains being obtained in which the carbon flux was redirected towards glycerol and 2,3-butanediol, a polyol with no sensorial impact in wines. These engineered wine yeasts have the potential to reduce the alcohol content of wine by 1 to 3% (v/v). However, the poor consumer acceptance of DNA recombinant technology in food is a major barrier to their commercialization. Consequently, there is a great interest to use alternative, non-GMO approaches to improve the properties of wine yeast strains.

Process for Obtaining Low Ethanol-Producing Variant Yeast Strains

Adaptive laboratory evolution (ALE) experiments, based on long term adaptation of yeast under environmental or metabolic constraints, has been used to improve yeast strains for biotechnological applications, including wine-making. Experimental evolutions using sodium chloride to generate osmotic stress have been used to study evolutionary processes, and in more applied work, to increase the tolerance of baking strains to freezing. NaCl-resistant evolved industrial strains were obtained, but the production of glycerol and ethanol by the evolved strains was not affected.

The present disclosure provides a process for obtaining a variant yeast strain. In the context of the present disclosure, a "variant yeast strain" is a natural (e.g., not genetically modified using recombinant DNA/RNA technology) yeast strain mutant which has been selected from an "ancestral" yeast strain using ALE (based on the salt described herein) to redirect carbon flux towards glycerol and, ultimately, reduce the production of ethanol during alcoholic fermentation. The ancestral yeast strain and the variant yeast strain are non-genetically modified organisms, e.g., their genomic content has not been altered by the introduction of exogenous nucleic acid molecules or the removal of endogenous nucleic acid molecules using genetic engineering techniques. In some embodiments, the alcoholic strength by volume (% v/v) of a fermented product (e.g., wine) obtained with the variant yeast strain is reduced when compared to the alcoholic strength by volume of a fermented product (e.g., wine) obtained with thee ancestral yeast strain, by between about 0.40% and 2.00% or by at least 0.40%, 0.45%, 0.50%, 0.60%, 0.70%, 0.80%, 0.90%, 1.00%, 1.10%, 1.20%, 1.30%, 1.40%, 1.50%, 1.60%, 1.70%, 1.80%, 1.90% or 2.00%. In alternative or complimentary embodiments, the ratio of the glycerol content of a fermented product (e.g., wine) obtained with the variant yeast strain to the glycerol content of a fermented product (e.g., wine) obtained with the ancestral yeast strain, is between 1.25 and 2.40 or at least 1.25 1.30, 1.35, 1.40, 1.45, 1.50, 1.55, 1.60, 1.70, 1.75, 1.80, 1.85, 1.90, 1.95, 2.00, 2.10, 2.15, 2.20, 2.25, 2.30, 2.35 or 2.40.

In the context of the present disclosure, during an alcoholic fermentation process, the "variant" yeast strain does not produce an amount of acetate, acetaldehyde and acetoin which can alter the organoleptic properties of the fermented product. In an embodiment, the content of acetate, acetaldehyde or acetoin in the fermented product obtained by using the variant yeast strain is either equal to or less than the corresponding content of acetate, acetaldehyde or acetoin in the fermented product obtained by using the ancestral yeast strain. In embodiments, the content of acetate, acetaldehyde or acetoin in the fermented product obtained by using the variant yeast strain is augmented when compared to the corresponding fermented product obtained using the ancestral yeast strain, this increase is equal to or less than 70%. In still some embodiments, the variant yeast strain can produce a greater amount of one or more compounds (such as 2,3-butanediol), when compared to the ancestral yeast strain, which does not impact the organoleptic properties of the fermented product. In some embodiments, the variant yeast strains are not more resistant to an hypersomotic shock caused by the salt than the ancestral yeast strain, but the variant yeast strains display better viability and a gain of fitness (when compared to the ancestral yeast strain) under conditions of hyperosmotic stress and carbon starvation.

In order to obtain the variant yeast strain, an ancestral yeast strain is submitted to ALE and is cultured in increasing salt concentrations. The salt used during ALE is capable of causing an hyperosmotic stress to the ancestral yeast strain. In the context of the present disclosure, the term hyperosmotic stress (also referred to as an hyperosmotic shock) is an increase in the solute (e.g., ionic) concentration around a yeast cell causing a rapid change in the movement of water across its cell membrane. In such conditions, an inhibition of the transport of substrates and cofactors into the cell can occur thus causing a shock. The salt in ALE can either be a single type of salt or a combination of salts capable of causing an hyperosmotic shock. The salt or the combination of salts used in the ALE described herein must be capable of providing a specific osmolality to the culture medium without inducing toxicity towards the parental strain. For example, in the context of the present disclosure, the cation of the salt (or combination of salts) used in ALE lacks toxicity with respect to the ancestral yeast strain when used at a concentration for providing an initial osmolality of at least 1 500 mmol/kg, at least 1 600 mmol/kg, at least 1 700 mmol/kg, at least 1 800 mmol/kg, at least 1 900 mmol/kg, at least 2 000 mmol/kg, at least 2 100 mmol/kg or at least 2 200 mmol/kg. The salt used in the processes described herein has a countercation which is different than sodium. For example, the salt can have a potassium countercation. Such salts include, but are not limited to KCl. Such salts exclude NaCl whose cation has been shown to cause toxicity to the ancestral yeast strain. Such salts also exclude sulfites, such as sodium sulfite ($Na_2SO_3$), which generate sodium cations and provide yeasts strains only modestly capable of decreasing the alcohol by volume content of fermented products.

In a first step, the process for obtaining the variant yeast strain includes culturing yeast strains in increasing salt concentrations. The ancestral yeast strain is used to inoculate (at a predetermined amount) a culture medium containing the salt at a specific concentration. The ancestral yeast strain is then cultured under conditions so as to achieve carbon or glucose depletion (e.g. also referred to as carbon starvation). Then, a pre-determined amount of the cultured yeasts is used to inoculate a fresh medium containing either the same salt concentration or a higher salt concentration. This cycle is repeated until the cultured yeasts reach a relatively stable phenotype with respect to glycerol and ethanol production in alcoholic fermentation. In some embodiments, this cycle is repeated for at least (about) 200, 250, 300, 250, 400, 450, 500, 550, 600, 650, 700 or 750 yeast generations. During the process, the osmolality of the medium used to culture the yeasts is progressively increased from about 1 5000 to about 5 000 mmol/kg. For example, in an embodiment, the osmolality during the initial phase of the process can be (about) at least 1 500 mmol/kg, at least 1 600 mmol/kg, at least 1 700 mmol/kg, at least 1 800 mmol/kg, at least 1 840 mmol/kg, at least 1 900 mmol/kg, at least 2 000 mmol/kg, at least 2 100 mmol/kg, at least 2 105 mmol/kg or at least 2 200 mmol/kg. Alternatively or in combination, the osmolality during the final phase of the first step of the process can be (about) at most 4 800 mmol/kg, at most 4 740 mmol/kg, at most 4 700 mmol/kg, at most 4 600 mmol/kg, at most 4 500 mmol/kg, at most 4 400 mmol/kg, at most 4 300 mmol/kg, at most 4 200 mmol/kg, at most 4 100 mmol/kg, at most 4 000 mmol/kg, at most 3 900 mmol/kg, at most 3 800 mmol/kg, at most 3 730 mmol/kg, at most 3 700 mmol/kg, at most 3 600 mmol/kg or at most 3 500 mmol/kg. In an embodiment, the osmolality during the first step of the process is increased from (about) 1 500 mmol/kg to (about) 4 800 mmol/kg, 4 740 mmol/kg, 4 700 mmol/kg, 4 600 mmol/kg, 4 500 mmol/kg, 4 400 mmol/kg, 4 300 mmol/kg, 4 200 mmol/kg, 4 100 mmol/kg, 4 000 mmol/kg, 3 900 mmol/kg, 3 800 mmol/kg, 3 730 mmol/kg, 3 700 mmol/kg, 3 600 mmol/kg or 3 500 mmol/kg. In another embodiment, the osmolality during the process is increased from (about) 1 600 mmol/kg to (about) 4 800 mmol/kg, 4 740 mmol/kg, 4 700 mmol/kg, 4 600 mmol/kg, 4 500 mmol/kg, 4 400 mmol/kg, 4 300 mmol/kg, 4 200 mmol/kg, 4 100 mmol/kg, 4 000 mmol/kg, 3 900 mmol/kg, 3 800 mmol/kg, 3 730 mmol/kg, 3 700 mmol/kg, 3 600 mmol/kg or 3 500 mmol/kg. In yet another embodiment, the osmolality during the first step of the process is increased from (about) 1 700 mmol/kg to (about) 4 800 mmol/kg, 4 740 mmol/kg, 4 700 mmol/kg, 4 600 mmol/kg, 4 500 mmol/kg, 4 400 mmol/kg, 4 300 mmol/kg, 4 200 mmol/kg, 4 100 mmol/kg, 4 000 mmol/kg, 3 900 mmol/kg, 3 800 mmol/kg, 3 730 mmol/kg, 3 700 mmol/kg, 3 600 mmol/kg or 3 500 mmol/kg. In still a further embodiment, the osmolality during the first step of the process is increased from (about) 1 800 mmol/kg to (about) 4 800 mmol/kg, 4 740 mmol/kg, 4 700 mmol/kg, 4 600 mmol/kg, 4 500 mmol/kg, 4 400 mmol/kg, 4 300 mmol/kg, 4 200 mmol/kg, 4 100 mmol/kg, 4 000 mmol/kg, 3 900 mmol/kg, 3 800 mmol/kg, 3 730 mmol/kg, 3 700 mmol/kg, 3 600 mmol/kg or 3 500 mmol/kg. In another embodiment, the osmolality during the first step of the process is increased from (about) 1 840 mmol/kg to (about) 4 800 mmol/kg, 4 740 mmol/kg, 4 700 mmol/kg, 4 600 mmol/kg, 4 500 mmol/kg, 4 400 mmol/kg, 4 300 mmol/kg, 4 200 mmol/kg, 4 100 mmol/kg, 4 000 mmol/kg, 3 900 mmol/kg, 3 800 mmol/kg, 3 730 mmol/kg, 3 700 mmol/kg, 3 600 mmol/kg or 3 500 mmol/kg. In still a further embodiment, the osmolality during the first step of the process is increased from (about) 1 900 mmol/kg to (about) 4 800 mmol/kg, 4 740 mmol/kg, 4 700 mmol/kg, 4 600 mmol/kg, 4 500 mmol/kg, 4 400 mmol/kg, 4 300 mmol/kg, 4 200 mmol/kg, 4 100 mmol/kg, 4 000 mmol/kg, 3 900 mmol/kg, 3 800 mmol/kg, 3 730 mmol/kg, 3 700 mmol/kg, 3 600 mmol/kg or 3 500 mmol/kg. In another embodiment, the osmolality during the first step of the process is increased from (about) 2 000 mmol/kg to (about) 4 800 mmol/kg, 4 740 mmol/kg, 4 700 mmol/kg, 4 600 mmol/kg, 4 500 mmol/kg, 4 400 mmol/kg, 4 300 mmol/kg, 4 200 mmol/kg, 4 100 mmol/kg, 4 000 mmol/kg, 3 900 mmol/kg, 3 800 mmol/kg, 3 730 mmol/kg, 3 700 mmol/kg, 3 600 mmol/kg or 3 500 mmol/kg. In yet another embodiment, the osmolality during the first step of the process is increased from (about) 2 100 mmol/kg to (about) 4 800 mmol/kg, 4 740 mmol/kg, 4 700 mmol/kg, 4 600 mmol/kg, 4 500 mmol/kg, 4 400 mmol/kg, 4 300 mmol/kg, 4 200 mmol/kg, 4 100 mmol/kg, 4 000 mmol/kg, 3 900 mmol/kg, 3 800 mmol/kg, 3 730 mmol/kg, 3 700 mmol/kg, 3 600 mmol/kg or 3 500 mmol/kg. In still a further embodiment, the osmolality during the first step of the process is increased from (about) 2 105 mmol/kg to (about) 4 800 mmol/kg, 4 740 mmol/kg, 4 700 mmol/kg, 4 600 mmol/kg, 4 500 mmol/kg, 4 400 mmol/kg, 4 300 mmol/kg, 4 200 mmol/kg, 4 100 mmol/kg, 4 000 mmol/kg, 3 900 mmol/kg, 3 800 mmol/kg, 3 730 mmol/kg, 3 700 mmol/kg, 3 600 mmol/kg or 3 500 mmol/kg. In another embodiment, the osmolality during the first step of the process is increased from (about) 2 200 mmol/kg to (about) 4 800 mmol/kg, 4 740 mmol/kg, 4 700 mmol/kg, 4 600 mmol/kg, 4 500 mmol/kg, 4 400 mmol/kg, 4 300 mmol/kg, 4 200 mmol/kg, 4 100 mmol/kg, 4 000 mmol/kg, 3 900 mmol/kg, 3 800 mmol/kg, 3 730 mmol/kg, 3 700 mmol/kg, 3 600 mmol/kg or 3 500 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 4 800 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 4 740 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 4 700 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 4 600 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 4 500 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 4 400 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 4 300 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 4 200 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 4 100 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 4 000 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 3 900 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 3 800 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 3 730 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 3 700 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 3 600 mmol/kg. In still another embodiment, the osmolality during the first step of the process is increased from (about) 1 500 mmol/kg, 1 600 mmol/kg, 1 700 mmol/kg, 1 800 mmol/kg, 1 840 mmol/kg, 1 900 mmol/kg, 2 000 mmol/kg, 2 100 mmol/kg, 2 105 mmol/kg or 2 200 mmol/kg to (about) 3 500 mmol/kg.

Broadly, the process comprises at least two phases. In a first phase, the yeasts are cultured at a relatively low salt concentration which is increased during culture. In a second phase, the yeasts are cultured at a higher and fixed salt concentration. During the process, the initial carbon source concentration in the culture medium (e.g., prior to culture) is high (at least 8% (w/v) with respect to total volume of the culture medium) in the culture medium so as to maintain the fermentative performances of the cultured yeast in the presence of, initially, a relatively high concentration of carbon. In the context of the present disclosure, in both phases, the yeasts are cultured until the carbon source is depleted (e.g., until a state of carbon starvation is reached) from the culture medium prior to proceeding to a further inoculation into a fresh medium.

During the first phase of the process, the yeasts are cultured in a first culture medium containing the salt and the carbon source. In the context of the present disclosure, the "first culture medium" refers to a culture medium that is used during the first phase of the process. The first culture medium can be any type of medium suitable for the growth of yeasts. Even though the first culture medium can be a solid medium, the first culture medium is preferably a liquid medium. Yeast-adapted medium include, but are not limited to, the Yeast Peptone Dextrose (YPD) medium or a defined/synthetic SD medium based a yeast nitrogen base medium. Optionally, the first culture medium can be supplemented with bacto-yeast extract and bactopeptone.

Initially, the concentration of the salt in the first culture medium is selected to increase the osmolality of the first culture medium (e.g., to reach at least at least 1 500 mmol/kg, at least 1 600 mmol/kg, at least 1 700 mmol/kg, at least 1 800 mmol/kg, at least 1 840 mmol/kg, at least 1 900 mmol/kg, at least 2 000 mmol/kg, at least 2 100 mmol/kg, at least 2 105 mmol/kg or at least 2 200 mmol/kg) and cause a reduction in growth (when compared to a yeast in the same medium without the salt) of the ancestral strain (which has not previously been cultured in the presence of such high salt concentration). This reduction in growth can be, for example, at least about 1.5, 2.0, 3.0, 4.0 fold or even more, when compared to the ancestral yeast strain cultured in similar conditions but in the absence of the salt. This salt concentration can correspond to 1.25 M when KCl is used as the salt to supplement a YPD medium and it provides an osmolality of about 2 105 mmol/kg. Thereafter, the yeasts are cultured in increasing salt concentrations. During the first phase, the salt concentration can be between about 1.25 M to less than about 2.4 M or at least about 1.25 M, 1.30 M, 1.40 M, 1.50 M, 1.60 M, 1.70 M, 1.80 M, 1.90 M, 2.0 M, 2.1 M, 2.2 M or 2.3 M. In an embodiment, the salt concentration in the first culture medium can serially be increased from about 1.25 M to about 1.30 M, from about 1.30 M to about 1.40 M, from about 1.40 M to about 1.50 M, from about 1.50 M to about 1.60 M, from about 1.60 M to about 1.70 M, from about 1.70 M to about 1.80 M, from about 1.80 M to about 1.90 M, from about 1.9 M to about 2.0 M, from about 2.0 M to about 2.1 M, from about 2.1 M to about 2.2 M, from about 2.2 M to about 2.3 M and from about 2.3 M to about 2.4 M. This serial increase can be made at predetermined intervals, for example at weekly intervals or at monthly intervals. In some embodiments, the first phase can comprise two sub-phases: a first sub-phase in which the salt concentration is increased weekly (for example by increasing the salt concentration from about 1.25 M to about 1.9 M) and a second sub-phase in which the salt concentration is increased monthly (for example by increasing the salt concentration from about 1.9 M to about 2.4 M).

The first culture medium also comprises an available carbon source, such as glucose. The initial concentration of the carbon source in the first culture medium is selected to allow the maintenance of good fermentative performances of the yeasts. For example, prior to the culture with the yeasts, the concentration of the carbon source in the first culture medium is at least 8% (w/v), between about 8% and about 14% (w/v) or between about 9.6% (w/v) and about 14% (w/v) with respect to the total volume of the culture medium. During the first phase, the initial carbon source concentration can be at least about 8.0%, 8.4%, 8.8%, 9.2%, 9.6%, 10.0%, 10.4%, 10.8%, 11.2%, 11.6%, 12.0%, 12.4%, 12.8%, 13.2%, 13.6% or 14%, preferably at least about 9.6%, 10.0%, 10.4%, 10.8%, 11.2%, 11.6%, 12.0%, 12.4%, 12.8%, 13.2%, 13.6% or 14.0% (w/v with respect to the total volume of the culture medium). In an embodiment, the carbon source concentration in the first culture medium can serially be decreased from about 14.0% to about 13.6%, from about 13.6% to about 13.2%, from about 13.2% to about 12.8%, from about 12.8% to about 12.4%, from about 12.4% to about 12.0%, from about 12.0% to about 11.6%, from about 11.6% to about 11.2%, from about 11.2% to about 10.8%, from about 10.8% to about 10.4%, from about 10.4% to about 10.0%, from about 10.0% to about 9.6%, from about 9.6% to about 9.2%, from about 9.2% to about 8.8%, from about 8.8% to about 8.4% and from about 8.4% to about 8.0%. This serial decrease can be made at pre-determined intervals, for example at weekly intervals or at monthly intervals. In some embodiments, the first phase can comprise two sub-phases: a first sub-phase in which the carbon source concentration is decreased weekly (for example by decreasing the carbon concentration from about 14% to about 9.6%) and a second sub-phase in which the carbon source concentration is increased monthly (for example by decreasing the carbon source concentration from about 9.6% to about 8.0%).

At the initial step of the first phase, the ancestral yeast strain can be first inoculated at a pre-determined concentration (e.g., an $OD_{600}$ of 1.0 for example) in the first culture medium. The ancestral strain is cultured under conditions so as to allow yeast growth (e.g., 28° C. under agitation). The yeasts are cultured in the first culture medium until the carbon source (usually glucose) has been metabolized (e.g., depleted). The time to reach carbon depletion will depend on the type of culture medium used, the amount of yeasts used to inoculate the culture medium, the incubation conditions as well as the initial amount of the carbon source. However, after about 4 to 7 generations (e.g., about a week), the carbon source in a YPD medium supplemented with 8% (w/w) glucose and inoculated at an $OD_{600}$ of 1.0 with cultured yeasts is considered depleted. In another example, after about 8 to 14 generations (e.g., about two weeks), the carbon source in a YPD medium supplemented with 14% (w/w) glucose and inoculated at an $OD_{600}$ of 1.0 with cultured yeasts is considered depleted.

During the first phase, once the carbon source has been depleted from the culture medium, the cultured yeasts can be maintained in a carbon starvation phase or can be inoculated into a fresh medium containing a higher salt concentration and a further source of available carbon. During the first phase, the increase in salt concentration between two culture media can be, for example, 0.05 M (initially) and 0.1 M (afterwards). In some embodiments, a more or less important increase in salt concentration can be made to achieve similar results. The first phase is maintained for at least about 175 days, at least about 25 weeks or at least about 100 generations. In an embodiment, the first phase is maintained until the growth rate of the cultured yeasts increases by at least about 5%, 6%, 7%, 8%, or 9% or 10% when compared to the growth rate of the cultured yeasts at the initiation of the first phase (when a reduction in growth rate is observed because of the presence of the salt).

When the salt concentration is increased in the first culture medium, a corresponding glucose concentration can be decreased in the first culture medium. For example, in an embodiment, when the salt concentration is increased by 0.1 M in the first culture medium, the glucose concentration can be decreased (prior to the culture) by 0.4% (w/v) with respect to the total volume of the first culture medium. In still another embodiment, when the salt concentration is increased by about 0.05 M in the first culture medium, the glucose concentration (prior to the culture) is decreased by about 0.2% (w/v) with respect to the total volume of the first culture medium.

Once the first phase of the process has been completed, in a second phase, the yeasts are cultured in a second culture medium containing the salt and the carbon source. In the context of the present disclosure, the "second culture medium" refers to a culture medium that is used during the second phase of the process. The second culture medium can be any type of medium suitable for the growth of yeasts. Even though the second culture medium can be a solid medium, the second culture medium is preferably a liquid medium. Yeast-adapted medium include, but are not limited to, the Yeast Peptone Dextrose (YPD) medium or a defined/synthetic SD medium based a yeast nitrogen base medium. Optionally, the second culture medium can be supplemented with bacto-yeast extract and bactopeptone.

During the second phase, the second culture medium has a salt concentration that is the same or higher than the first culture medium at the end of the first phase. However, during the second phase, the salt concentration remains the same and does not increase. In an embodiment, the salt concentration of the second culture medium can be about 2.4 M. In some embodiment, the second culture medium has an osmolality of at most about 4 800 mmol/kg, at most about 4 740 mmol/kg, at most about 4 700 mmol/kg, at most about 4 600 mmol/kg, at most about 4 500 mmol/kg, at most about 4 400 mmol/kg, at most about 4 300 mmol/kg, at most about 4 200 mmol/kg, at most about 4 100 mmol/kg, at most about 4 000 mmol/kg, at most about 3 900 mmol/kg, at most about 3 800 mmol/kg, at most about 3 730 mmol/kg, at most about 3 700 mmol/kg, at most about 3 600 mmol/kg or at most about 3 500 mmol/kg. mmol/kg.

As indicated above, the second culture medium also comprises a carbon source, such as glucose. The initial concentration of the carbon source in the second culture medium is selected to allow the maintenance of good fermentative performances of the yeasts. In an embodiment, the initial concentration of the carbon source in the second culture medium is equal to or lower than the initial concentration of the carbon source in the first culture medium at the end of the first phase of the process. Further, the initial glucose concentration (prior to culture) in the second culture medium remains the same during the second phase. In an embodiment, prior to the culture with the yeasts, the concentration of glucose in the second culture medium is between about 8% and about 14% (w/v), preferably between about 8% and about 10% (w/v) and even more preferably about 8% (w/v with respect to the total volume of the second culture medium). In an embodiment, the salt concentration of the second culture medium is about 2.4 M. When KCl is used at such concentration to supplement a YPD medium, this corresponds to an osmolality of about 3 730 mmol/kg.

During the second phase, the first cultured yeast strain (e.g., a yeast strain that has been submitted and completed the first phase of the process) is first inoculated at a predetermined concentration (e.g. an $OD_{600}$ of 1.0) in the second culture medium containing the salt as well as the carbon source. The yeast strain is cultured under conditions so as to allow yeast growth (e.g., 28° C. under agitation). The yeasts are cultured in the second culture medium until the carbon source (usually glucose) has been metabolized (e.g., depleted). The time to reach carbon depletion will depend on the type of culture medium used, the amount of yeasts used to inoculate the culture medium, the incubation conditions as well as the initial amount of the carbon source. However, after about 4 to 7 generations (e.g., about a week), the carbon source in a YPD medium supplemented with about 8% (w/w) glucose and inoculated at an $OD_{600}$ of 1.0 with cultured yeasts is considered depleted.

During the second phase, once the carbon source has been depleted from the culture medium, the cultured yeasts are either maintained in a glucose starvation state or inoculated into a fresh medium containing the same salt concentration and the same carbon source concentration than the previous medium. During the second phase, the salt concentration can be about 2.4 M and the glucose concentration can be about 8.0% (w/w). In embodiments, the second phase is maintained for at least about 553 days, at least about 79 weeks and/or at least about 200 generations. In an embodiment, the second phase lasts until the cultured yeast strain exhibit a stable phenotype with respect to glycerol and ethanol production in the absence of the salt stress.

The first and second culture medium can have the same base medium and differ only with respect to the salt, the salt concentration, the carbon source and/or the carbon source concentration. Alternatively, the first and second can have different base medium.

At the end of the second phase of the process, it is expected that the cultured yeast strains (now referred to as variant yeasts strains) have the ability of producing more glycerol during an alcoholic fermentation than the ancestral yeast strain. For example, in some embodiments, the ratio of the glycerol content of a fermented product (e.g., wine) obtained with variant yeast strains to the glycerol content of a fermented product (e.g., wine) obtained with the ancestral yeast strain, is between 1.25 and 2.40 or at least about 1.25, 1.30, 1.35, 1.40, 1.45, 1.50, 1.55, 1.60, 1.70, 1.75, 1.80, 1.85, 1.90, 1.95, 2.00, 2.10, 2.15, 2.20, 2.25, 2.30, 2.35 or 2.40. It is also expected that the variant yeast strains have the ability of producing less ethanol during an alcoholic fermentation than the ancestral yeast strain. For example, in some embodiments, the alcoholic strength by volume (% v/v) of a fermented product (e.g., wine) obtained with the variant yeast strain is reduced, when compared to the alcoholic strength by volume of a fermented product (e.g., wine) obtained with thee ancestral yeast strain, by at least 0.40% or between about 0.40% and 2.00% or by at least about 0.40%, 0.45%, 0.50%, 0.60%, 0.70%, 0.80%, 0.90%, 1.00%, 1.10%, 1.20%, 1.30%, 1.40%, 1.50%, 1.60%, 1.70%, 1.80%, 1.90% or 2.00%. In some embodiments, the variant yeast strain can produce a greater amount of one or more compounds (such as 2,3-butanediol), when compared to the ancestral yeast strain, which does not impact the organoleptic properties of the fermented product.

The variant yeasts strains can optionally be further submitted to conventional breeding (which excludes genetic engineering manipulations) to further increase their ability to produce glycerol, decrease their ability to produce ethanol during an alcoholic fermentation and/or produce inter-species hybrid having a similar phenotype. Conventional breeding conducted with yeasts of the same species (e.g., intra-species breeding) or with yeasts of different species (e.g., inter-species breeding). Such breeding techniques are known to those skilled in the art and usually include (i) the production of haploid yeast spores from a selected variant yeast strain, (ii) the selection of haploid strains having the desired phenotype (e.g., an increased capacity in producing glycerol and/or a decreased capacity of producing ethanol during an alcoholic fermentation for example) and (iii) the mating of the selected haploid strains to obtain stable hybrid (e.g., diploid) strain and the selection of a hybrid strain having the desired phenotype (e.g., an increased capacity in producing glycerol, a decreased capacity of producing ethanol during an alcoholic fermentation and/or an inter-species hybrid having the desired (stable) phenotype). This optional breeding step can be used to obtain $1^{st}$ generation hybrids (e.g., usually referred to as H1), $2^{nd}$ generation hybrids (e.g., usually referred to as H2) and even $3^{rd}$ generation hybrids (e.g., usually referred to as H3). As indicated above, the breeding step can include the generation of intra-species and inter-species hybrids).

Prior to or after the breeding, the variant yeast strain can optionally be submitted to a further step for determining their ability to conduct cellular respiration. Variant yeast strains capable of cellular respiration are considered to be useful for wine-making applications.

The process described herein can be apply to yeasts and is especially useful for the generation of variant yeast strains destined to be used in alcoholic fermentations. Exemplary yeasts includes, but are not limited to *Saccharomyces* sp. (for example, from the genus *Saccharomyces arboricolus, Saccharomyces eubayanus, Saccharomyces bayanus, Saccharomyces cerevisiae, Saccharomyces kudriadzevii, Saccharomyces mikatae, Saccharomyces paradoxus, Saccharomyces pastorianus, Saccharomyces carsbergensisand Saccharomyces uvarum.*), *Brettanomyces* sp. (Teleomorph *Dekkera* sp.), *Candida* (Teleomorphs for different species from several genera including *Pichia* sp., *Metschnikowia* sp., *Issatchenkia* sp., *Torulaspora* sp. and *Kluyveromyces* sp.), *Kloeckera* sp. (Teleomorph *Hanseniaspora* sp.), *Saccharomycodes* sp., *Schizosaccharomyces* sp. and/or *Zygosaccharomyces* sp as well as inter-species hydrids derived from any one of these yeast species.

Variant Yeast Strains and their Use in Alcoholic Fermentation

The present disclosure also concerns the variant yeast strain obtained by the process described herein. As described herein, the "variant yeast strain", during an alcoholic fermentation, produces more glycerol and less ethanol than its corresponding ancestral yeast strain and is obtained by the process described herein. As such, the fermented products obtained using the variant yeast strain has less ethanol than the fermented products obtained using the ancestral yeast strain. For example, the alcoholic strength by volume (% v/v) of a fermented product (e.g., wine) obtained with the variant yeast strain can be reduced, when compared to the alcoholic strength by volume of a fermented product (e.g., wine) obtained with thee ancestral yeast strain, by between about 0.40% and about 2.00% or by at least about 0.40%, 0.45%, 0.50%, 0.60%, 0.70%, 0.80%, 0.90%, 1.00%, 1.10%, 1.20%, 1.30%, 1.40%, 1.50%, 1.60%, 1.70%, 1.80%, 1.90% or 2.00%. Further, the fermented products obtained using the variant yeast strain has more glycerol than the fermented products obtained using the ancestral yeast strain. For example, the ratio of the glycerol content of a fermented product (e.g., wine) obtained with the variant yeast strain to the glycerol content of a fermented product (e.g., wine) obtained with the ancestral yeast strain, is between about 1.25 and about 2.40 or at least about 1.25

1.30, 1.35, 1.40, 1.45, 1.50, 1.55, 1.60, 1.70, 1.75, 1.80, 1.85, 1.90, 1.95, 2.00, 2.10, 2.15, 2.20, 2.25, 2.30, 2.35 or 2.40. In some embodiment, the "variant" yeast strain, during an alcoholic fermentation, does not produce an amount of acetate, acetaldehyde and acetoin (when compared to the "ancestral yeast strain") which can alter the organoleptic properties of the fermented product. For example, the content of acetate, acetaldehyde or acetoin in the fermented product obtained by using the variant yeast strain can be either equal to or less than the corresponding content of acetate, acetaldehyde or acetoin in the fermented product obtained by using the ancestral yeast strain. Alternatively, the content of acetate, acetaldehyde or acetoin in the fermented product obtained by using the variant yeast strain can be augmented when compared to the corresponding fermented product obtained using the ancestral yeast strain. In still some embodiments, the variant yeast strain can produce a greater amount of one or more compounds (such as 2,3-butanediol), when compared to the ancestral yeast strain, which does not impact the organoleptic properties of the fermented product. In some embodiments, the variant yeast strains are not more resistant to an hyperosmotic shock caused by the salt than the ancestral yeast strain, but the variant yeast strains display better viability and a gain of fitness (when compared to the ancestral yeast strain) under conditions of hyperosmotic stress and carbon starvation.

One of the exemplary variant yeast strain of the present disclosure has been deposited at Institut Pasteur, on Jan. 9, 2014, under accession number CNCM I-4832. Another exemplary variant yeast strain of the present disclosure has been deposited at Institut Pasteur, on Oct. 18, 2012 under accession number CNCM I-4684. A further exemplary variant yeast strain of the present disclosure has been deposited at Institut Pasteur, on Oct. 18, 2012 under accession number CNCM I-4685. In yet another exemplary variant yeast strain of the present disclosure has been deposited at Institut Pasteur, on Jan. 28, 2015 under accession number CNCM I-4952.

The present disclosure also concerns the use of the variant yeast strain during an alcoholic fermentation process in which it is warranted to limit the alcohol content of the final fermented product. In the process for making a fermented product having an alcoholic content, the variant yeast strain is placed in contact with a fermentable source of nutrients and the fermentation is conducted in conditions allowing the completion of the alcoholic fermentation. The variant yeast strains are especially useful in processes for making wines (e.g., red, white, rosé, sparkling or fortified wine). In such embodiment, the variant yeast strain is placed into contact with a grape must and the fermentation is conducted in conditions allowing the completion of the alcoholic fermentation. Optionally, the variant yeast strain can be provided in a dried formulation and submitted to a rehydration step prior to the fermentation. In another embodiment, the variant yeast strain can be provided in a liquid formulation and submitted to a dilution step and/or a thawing step prior to fermentation. In an embodiment, only the variant yeast strain is used to complete the alcoholic fermentation. Alternatively, the variant yeast strain can be admixed with other yeast strain to ferment. In some embodiments, when the fermented product is a white wine, the fermentation is conducted at a temperature below about 25° C., usually at about between about 20° C. and about 24° C. In other embodiments, when the fermented product is a red wine, the fermentation is conducted at a temperature equal to or higher than about 25° C., for example, at a temperature between about 25° C. and about 30° C., and in some embodiments, at a temperature between about 25° C. and about 28° C. (e.g., 28° C. for example). In some variant yeast strains described herein, a metabolic shift towards the production of glycerol has been observed when the yeasts are incubated at a temperature higher than about 24° C. In such variant yeasts strain, the maximal reduction in ethanol production was observed at about 28° C. As such, some of the variant yeasts strains described herein are especially suited for providing a lower alcohol content in red wines. The resulting wines can optionally be filtered and bottled, as it is currently done in the art.

The variant yeast strains can be used to ferment the must of different grape species (alone or in combination), such as *Vitis vinifera*, as well as hybrid grape species combining one of more of *V. labrusca, V. aestivalis, V. ruprestris, V. rotundifolia* and *V. riparia*. The variant yeast strains can be used to ferment the must of different grape varieties (alone or in combination) used to make red, white, rosé, sparkling or fortified wine. Grape varieties used to make red wines include, but are not limited to, Aghiorghitiko, Aglianico, Aleatico, Alicante Bouschet, Aramon, Baga, Barbera, Blaufrankisch, Cabernet Franc, Cabernet Sauvignon, Canaiolo, Carignan, Carmenere, Cinsaut, Dolcetto, Dornfelder, Elbling, Freisa, Gaglioppo, Gamay, Grenache/Garnacha, Grignolino, Malbec, Mavrud, Melnik, Merlot, Mondeuse (Refosco), Montepulciano, Nebbiolo, Negroamaro, Nero d'Avola, Nielluccio, Periquita, Petit and Gros Manseng, Petit Verdot, Petite Sirah, Sagrantino, Sangiovese, Saperavi, Saint Laurent, Syrah/Shiraz, Tannat, Tempranillo, Teroldego, Tinta Barroca, Tinto Cao, Touriga Francesa, Xinomavro and/or Zinfandel. Grape varieties used to make white wines include, but are not limited to, Airen, Albana, Albarino (Alvarinho), Aligote, Arneis, Bacchus, Bombino, Chardonnay, Chasselas, Chenin Blanc, Clairette, Ehrenfelser, Elbling, Ezerjo, Fernão Pires, Furmint, Garganega, Gewürztraminer, Grechetto, Greco, Grillo, Grüner Veltliner, Hárslevelú, Huxelrebe, Inzolia, Iona, Jacquère, Kerner, Listan, Macabeo, Malvasia, Marsanne, Melon de Bourgogne, Optima, Palomino, Parelleda, Pedro Ximenez, Picpoul, Pinot Blanc, Pinot Gris/Grigio, Reichensteiner, Riesling, Rkatsiteli, Robola, Roditis, Sauvignon Blanc, Savagnin, Scheurebe, Semillon, Silvaner, Tocai Friulano, Torrontes, Trebbiano, Ugni-Blanc, Verdejo, Verdelho, Verdicchio, Vermentino, Vernaccia di San Gimignano, Viognier, Welschriesling and/or Xarel-lo.

Some of the advantages of using the variant yeast strain in processes for making a fermented product (such as wine) include, but are not limited to, the avoidance of using genetically-modified yeast strains, the avoidance of using mechanical de-alcoholisation procedures (e.g., reverse osmosis, nano-filtration or distillation) and/or the applicability to various grape varieties, irrelevant to the initial sugar content. As such, the process for obtaining a fermented product having alcohol (such as a wine) can exclude the use of genetically-modified yeast strain and/or the use of mechanical de-alchololisation procedures.

The variant yeast strains are especially useful in processes for making wines (e.g., red, white, rosé, sparkling or fortified wine). In such embodiment, the variant yeast strain is placed into contact with a wine must and the fermentation is conducted in conditions allowing the completion of the alcoholic fermentation. Optionally, the variant yeast strain can be submitted to a rehydration step prior to the fermentation. In an embodiment, only the variant yeast strain is used to complete the alcoholic fermentation. Alternatively, the variant yeast strain can be admixed with other yeast strain to ferment. In some embodiments, when the fermented product is a white wine, the fermentation is conducted at a temperature below about 25° C., usually at about between about 20° C. and about 24° C. In other embodiments, when the fermented product is a red wine, the fermentation is conducted at a temperature equal to or higher than about 25° C., for example, at a temperature between about 25° C. and about 30° C., and in some embodiments, at a temperature between about 25° C. and about 28° C. (e.g., 28° C. for example). In some variant yeast strains described herein, a metabolic shift towards the production of glycerol has been observed when the yeasts are incubated at a temperature higher than about 24° C. In such variant yeasts strain, the maximal reduction in ethanol production was observed at about 28° C. As such, some of the variant yeasts strains described herein are especially suited for providing a lower alcohol content in red wines. The resulting wines can optionally be filtered and bottled, as it is currently done in the art.

The variant yeast strains can also be used to ferment the cereal-derived starch (e.g. malted cereal) in brewed application for making beer.

The present invention will be more readily understood by referring to the following examples which are given to illustrate the invention rather than to limit its scope.

Example I

KCl-Based Adaptive Laboratory Evolution

Yeast Strain and Growth Conditions.

The wine yeast strain S. cerevisiae Lalvin EC1118® was used as the ancestral strain. Prior to ALE, strains were propagated in rich YPD medium (1% bacto yeast extract (DB), 2% bactopeptone (DB), 2% glucose; Legallais) or in synthetic SD medium (0.67% Difco yeast nitrogen base without amino acids (DB), 2% glucose) and maintained on YPD plates (2% agar) at 4° C. or stored at −80° C. in 20% glycerol.

KCl Resistance Assay.

EC1118 was grown in 60 mL YPD with KCl in concentrations varying from 0.5 to 3M, at 28° C., under agitation. Optical density at 600 nm was measured each 6 hours until 240 hours and growth was compared for the different conditions.

Adaptive Laboratory Evolution (ALE).

Adaptive evolution was based on a long-term serial transfer procedure using KCl as stress inducer. The strain EC1118 was cultured overnight at 28° C. in 5 mL of YPD, and the resulting cell suspension was used to inoculate capped tubes (13 mL), each containing 5 mL medium with 1% bacto yeast extract, 2% bactopeptone, 14% glucose and 1.25M KCl (Sigma-Aldrich). Duplicate evolution experiments and also a control without stress were performed. The cultures were incubated at 28° C. under agitation at 225 rpm. After 7 days, corresponding to about 5 generations, the optical density of the culture at 600 nm ($OD_{600}$) was measured and an aliquot was used to inoculate a fresh medium such that the $OD_{600}$ was 1. Such serial transfers were repeated for 450 generations. Every 50 generations, 1 mL samples of the evolving population were taken and stored at −80° C. in 20% glycerol for subsequent analysis.

After 7 days of culture, the cultures were inoculated in a YPD medium containing 13.6% glucose and 1.30 M KCl. Then, each week, the subcultures were inoculated in a medium in which the KCl concentration was increased by a further 0.1 M and the glucose concentration was decreased by a further 0.4%. This phase lasted between $d_7$ and $d_{49}$.

Afterwards every 4 weeks, the KCl concentration was increased by 0.1 M and the glucose was decreased by 0.4%. This phases lasted between $d_{49}$ and $d_{728}$.

Wine Fermentation (Laboratory Scale).

Batch fermentation experiments were carried out in synthetic medium (MS), which mimics a standard grape juice. MS medium was prepared as described by Bely et al. with the following modifications: 260 g/L glucose, 210 mg/L available nitrogen, 7.5 mg/L ergosterol, 0.21 g/L Tween® and 2.5 mg/L oleic acid (MS210 medium). Fermentations in grape must were carried out in the same conditions, using Chardonnay-Coursan 2011 previously flash pasteurized. The fermentations were performed in 330 mL fermenters containing 300 mL medium, inoculated with $0.5 \times 10^6$ cells per mL and incubated at 28° C. with continuous stirring (350 rpm). To study the metabolic flexibility of the evolved and ancestral strains, different temperatures were used (16, 20, 24, 32 and 34° C.). Fermentation kinetics was monitored by calculation of the amount of $CO_2$ released determined by weighing the fermenters manually. All fermentation experiments were performed in triplicate. Extracellular metabolites and volatile compounds were assayed at the end of the fermentation.

Wine Fermentation (Pilot Scale).

Pilot-scale fermentations were performed in 1 hL cylindrical stainless-steel tanks with Grenache variety grape must. This grape must contains 269 g/L sugars and 186 mg/L nitrogen and was flash pasteurized and stored at 2° C. before fermentation. Grenache must was inoculated at 25 g/hL with EC1118 and K300.1(b) active dry yeasts (Lallemand, Toulouse, France). $CO_2$ production was determined using a Brooks 5810 TR series gas flowmeter (Brooks Instrument, PA, USA), as described by Aguera and Sablayrolles. Fermentations were carried out under isothermal conditions at 28° C. Dissolved oxygen was added during fermentation to limit the risk of stuck fermentation. A transfer of 4 mg/L, 7 mg/L and 10 mg/L oxygen was performed when the $CO_2$ released reached 7.2 g/L, 13.5 g/L and 45 g/L respectively. Nitrogen (72 mg/L) was added under the form of 15 g/hL DAP and 30 g/hL FermaidE at 45 g/L of $CO_2$ released.

Viability of Evolved Strains.

Ancestral and evolved cells were grown in 50 mL of YPGluKCl (1% bacto yeast extract, 2% bactopeptone, 8% glucose and 2.4 M KCl) inoculated at 0.1 $OD_{600}$/mL from an overnight preculture in YPD. The size of the cell population, extracellular metabolites and viability were followed for 7 days. The assays were performed in triplicate. Viability was determined using a flow cytometer (Accuri, BD Biosciences) to count 20 000 cells diluted and washed in 300 μL 1×PBS (137 mmol/L NaCl (Sigma-Aldrich), 2.7 mmol/L KCl, 100 mmol/L $Na_2HPO_4$ (Sigma), 2 mmol/L $KH_2PO_4$ (Sigma), pH 7.5) with 3 μL of propidium iodide (Calbiochem) previously diluted to 0.1 mg/mL in sterile water.

Analytical Methods.

Cell densities were determined by measuring the $OD_{600}$ with a Secomam UVILine 9400 or by using a Coulter ZBI cell counter linked to a C56 Channelyzer fitted with a probe with a 100 mm aperture (Beckman Coulter). Dry weight was determined gravimetrically by filtering 10 mL of sample (pore size 0.45 μm, Millipore) and drying the sample for 24 h at 100° C. Extracellular glucose, glycerol, ethanol, pyruvate, succinate and acetate concentrations were determined by high-pressure liquid chromatography (HPLC), using an HPX-87H ion exclusion column (Bio-Rad). Volatile compounds (acetoin and 2,3-butanediol) were assayed by gas chromatography (GC). Acetoin and butanediol were extracted into chloroform according to the Hagenauer-Hener protocol with the following modifications: 1 mL of hexanol (Sigma) as an internal standard (1:1000 v/v) in 10% ethanol (VWR) was added to 1 mL of sample. The organic phase was dried and 1 µL was injected into a 30 m megabore column (DBWAX, JandW Scientific) on a GC apparatus HP 6890. The acetaldehyde concentrations were determined enzymatically according to the Lundquist method. For pilot-scale experiments, glucose and fructose concentrations were determined enzymatically. The ethanol concentration was determined by measuring density, the volatile acidity by the bromophenol blue method, the $SO_2$ concentration by iodometry and total acidity by titration. The osmolality was measured using a Vapro 5520 device (Wescor) with a sample volume of 10 µL.

Adaptive Evolution Under Hyperosmotic KCl-Medium and Isolation of High-Glycerol-Producing Evolved Strains.

To evolve strain EC1118, batch cultures in YPD 8% glucose with a gradual increase of osmotic stress were performed. KCl stress was chosen because it generates osmotic and salt stress but unlike NaCl does not cause cation toxicity. A high sugar concentration (8%) was used to maintain good fermentative performances of the evolved strain in rich sugar medium. In preliminary experiments, the effect of various KCl concentrations was tested on EC1118 growth and it was found that the addition of 1.25 M KCl on YPD 8% glucose reduced the growth of EC1118 four times (data not shown). The adaptive laboratory evolution (ALE) experiments were started in YPD 8% glucose containing 1.25 M KCl. The osmolality of this medium is 2 105 mmol/kg, compared to 480 mmol/kg for YPD 8% glucose. The concentrations of KCl were progressively increased up to 2.4 M, corresponding to an osmolality of 3730 mmol/kg and maintained at that level thereafter. Duplicate ALE experiments were performed for each condition and one control ALE experiment, without osmotic stress, was done.

Samples collected after 100, 200, 300 and 400 generations were first analysed to monitor the dynamics of each evolution experiment. Yeast cells were plated on YPD and the populations obtained were characterized during fermentation of the synthetic must MS210 at 28° C. The glycerol concentration in the growth medium was measured at the end of the fermentation as a first indicator of the success or failure of the adaptation. Adaptation on KCl medium generated evolved populations with increased glycerol production during wine fermentation (FIG. 1) whereas no increase of glycerol was observed in the control experiment (evolution of EC1118 without stress). A similar increase in glycerol production was observed in the two parallel KCl experiments (a) and (b). In fermentations with both (a) and (b) lineages, the concentration of glycerol produced by fermentation reached 12 g/L for evolved populations at 200 generations; the value for the ancestral EC1118 was 8.5 g/L. The KCl-ALE experiment was pursued for 450 generations (total duration of almost 2 years), but only little variation in glycerol production was observed after 200 generations (data not shown).

First Characterization of the Evolved Strains During Wine Fermentation.

After several generations, due to the natural accumulation of mutations, a non-homogeneous population of yeasts should be present in samples obtained from ALE experiments. Yeast populations sampled after different times of the KCl-ALE experiment were subcultured on YPD. These subclones, hereafter called evolved strains, were characterized during wine fermentation on MS210 medium (FIG. 1). All the evolved strains obtained after 200 generations produced more glycerol than the ancestral strain; glycerol production remained stable after 200 generations. Consistent with the re-routing of carbons and NADH oxidation resulting from increased glycerol production, all evolved strains showed a reduced ethanol yield. The ethanol yield was between 0.440 and 0.450 for the evolved strains and 0.464 for the reference ancestral strain (FIGS. 1 A and B). The evolved mutants showed reduced sugar consumption (FIGS. 1 C and D). Thus, there was a correlation between high glycerol yield, reduced ethanol yield and diminution of fermentative properties. A detailed study of six KCl-evolved strains from populations isolated after 200, 250 and 300 generations, including three from lineage (a): K200.1(a), K250.1(a), K300.2(a) and three from lineage (b): K200.1(b), K250.3(b), K300.1(b) was undertaken. Yeast strain K300.1 (b) (also named Lowa3 herein) was registered under CNCM I-4684 as a biological deposit in the Collection National de Cultures de Microorganismes (CNCM) of the Institut Pasteur on Oct. 18, 2012. Yeast strain K250.3(b) (also named Lowa2 herein) was registered under CNCM I-4685 as a biological deposit in the Collection National de Cultures de Microorganismes (CNCM) of the Institut Pasteur on Oct. 18, 2012.

High-Glycerol-Producing Strains Survive Better in Conditions of Osmotic Stress and Carbon Restriction.

Figure 2:
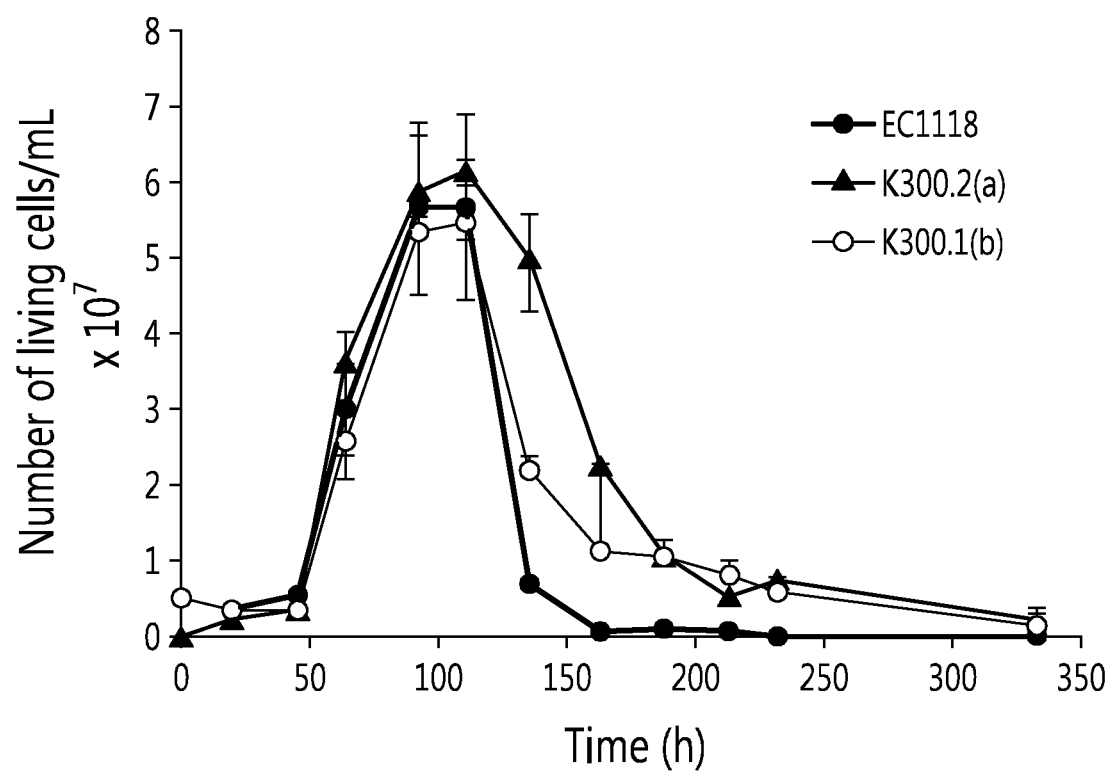
FIG. 2 shows the selective advantage of the evolved strains. Viability of EC1118 (•, black line), K300.2(a) (▲, dark grey line) and K300.1(b) (○, light gray line) during culture in YPD+8% glucose and 2.4 M KCl at 28° C. Results are shown as the number ($\times 10^7$) of living cells/mL in function of time (hours). Sugar exhaustion is observed after 100 hours. Each point includes the measured value as well as the standard deviation.

The resistance of the evolved strains to hyperosmotic stress was assessed by growth on KCl, NaCl or sorbitol SD plates. In these conditions, no significant differences in growth were observed between EC1118 and the evolved strains (FIG. 2): under the conditions of the ALE experiment (YPD 80 g/L glucose, 2.4 M KCl), the specific growth rate and maximal cell number reached by the evolved strains were similar to those of the ancestral strain. Therefore, yeast cells that evolved in these conditions did not display growth adaptation to osmotic stress. It was then examined whether other components of fitness, such as viability, had been improved during the evolution experiment. Cell viability was monitored during culture involving a 7-day transfer cycle in the conditions of the evolution experiment (YPD 80 g/L glucose, 2.4 M KCl). After complete glucose exhaustion (about 4 days), the evolved mutants survived better than the ancestral strain. After 7 days (corresponding to the time of transfer to fresh medium during the evolution experiment), almost all EC1118 cells had died, whereas the number of viable cells of the evolved mutants was considerably higher (FIG. 2). The viability of the evolved mutants at 7 days correlated with glycerol production at the same time-point (data not shown). Therefore, the main adaptation to the selective pressure put on yeast cells during the adaptive evolution experiment appeared to be improved survival in conditions of salt stress and carbon restriction.

Characterization of the Selected KCl-Evolved Strains During Wine Fermentation.

The characteristics of the six selected KCl-evolved strains and the ancestral strain were studied in detail during wine fermentation in anaerobic batch cultures on MS medium. All the strains were able to complete the fermentation, although the duration of the fermentation differed between the evolved strains (Table 1). Two evolved strains, K200.1(b) and K300.1(b), consumed all the sugar in less than two weeks, like the ancestral strain, whereas one month or more was required for the four other evolved strains (sugar was completely exhausted only after 40 days by K250.1(a) and K300.2(a)).

Figure 3A:
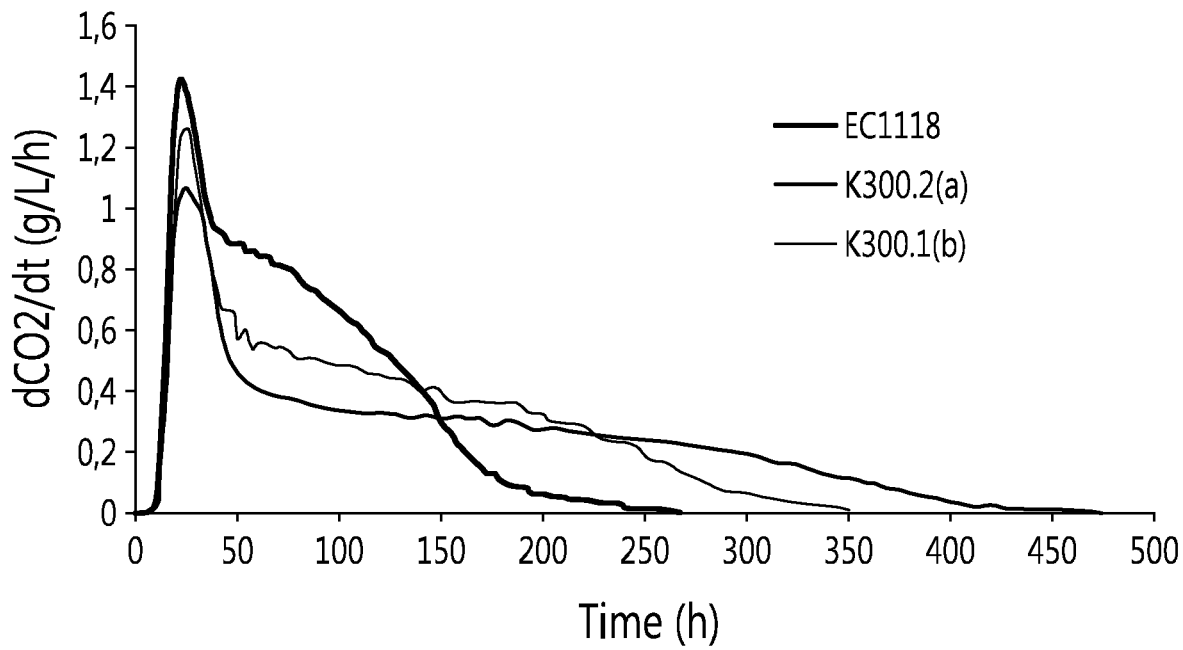
FIG. 3 illustrates the fermentation performances (A) and cell population (B) of the ancestral strain EC1118 (•, black line) and the evolved strains K300.2(a) (▲, dark grey line) and K300.1(b) (○, light grey line) on MS210 medium, 260 g/L glucose, at 28° C. Results in panel A are provided as $dCO_2/dt$ (g/l/H) in function of time (hours). Results in panel B are provided as the number of cells ($\times 10^7$)/mL in function of time (hours) and include the standard deviation.
Figure 3B:
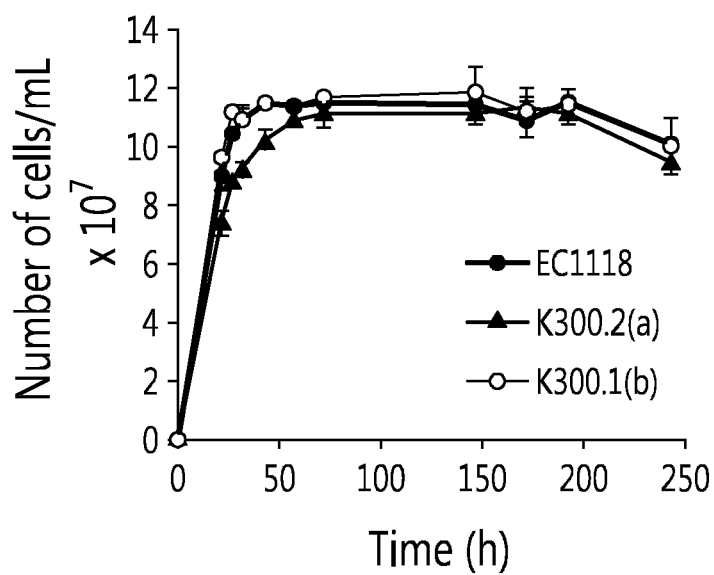

The fermentation rate of two evolved strains having distinct fermentation capacity, K300.2(a) and K300.1(b), is shown in FIG. 3A. The evolved strains exhibited an overall decrease of fermentation performance in comparison to the ancestral strain, which is consistent with the reduced sugar consumption observed before, but were nevertheless able to complete the fermentation. Final cell population was the same between ancestral and these two evolved strains despite that K300.2(a) showed a slower growth than K300.1(b) (FIG. 3B).

The concentration of the most abundant by-products was determined after 30 days of fermentation (Table 1). Carbon and redox balances were close to 100% for all strains. All evolved strains produced glycerol at concentrations 48 to 67% higher than that produced by EC1118, and the ethanol content in the synthetic wines was 0.45 to 0.80% (v/v) lower. The evolved strains also produced greater amounts of succinate, 2,3-butanediol and acetaldehyde than the ancestral strain. Succinate production by K200.1(a) and K300.2(a) was 22% and 88.9% higher, than that by EC1118; the production of acetaldehyde by K200.1(a) and K300.2(a) was 45.5% to 181.8% higher, respectively, and that of 2,3-butanediol by 93% to 255.6% higher. The concentration of these compounds was also increased in strains overexpressing GPD1 coding for the glycerol 3-P dehydrogenase, in which the carbon flux is redirected towards glycerol formation at the expense of ethanol (Michnick et al., Remize et al., Cambon et al.). By contrast, unlike previously described engineered strains, no significant changes in the production of acetate and acetoin by the evolved strains was observed.

Although similar phenotypes were observed for the two replicates, lineage (b) was characterized by slightly greater glycerol production and better fermentative performances. K300.1(b) was the most promising evolved strain obtained in terms of fermentation capacity and production of glycerol, succinate, 2,3-butanediol and ethanol.

Metabolic Properties of the Evolved Strain K300.1(b) at Various Temperatures on Synthetic and Natural Grape Musts.

Wine can be produced in a large range of fermentation temperatures, usually from 16° C. (for white wines) to 28° C. and more (for red wines). The metabolic properties of the ancestral strain and the evolved strain K300.1(b) were compared over a wide range of temperatures (16, 20, 24, 28, 32 and 34° C.) in MS210 medium containing 260 g/L sugars. For temperatures between 16 and 28° C., both strains consumed all or most of the sugar, while for the two highest temperatures, a residual sugar concentration of 43 and 53 g/L for EC1118 and 47 and 59 g/L for K300.1(b) was observed at 32 and 34° C. respectively.

The yields of by-products were determined after 30 days of fermentation (FIG. 4). At all temperatures, K300.1(b) was clearly differentiated from EC1118 on the basis of high glycerol, high succinate and low ethanol yields. The yields of glycerol and succinate increased with increasing temperature, whereas the ethanol yield decreased. The differences between temperatures were larger for K300.1(b) than for EC1118, in particular for the three highest temperatures. The ethanol content was reduced by 0.14% (v/v), 0.18% (v/v) and 0.24% (v/v) at 16° C., 20° C. and 24° C. and by 0.61% (v/v), 0.80% (v/v), 0.87% (v/v) at 28° C., 32° C. and 34° C. respectively with the evolved strain compared to EC1118. Therefore, a metabolic shift was observed between 24° C. and 28° C. To examine whether a similar behavior can be observed on natural must, fermentation was carried out in Chardonnay-Coursan, under similar conditions, at 24° C. and 28° C. Under these conditions, the ethanol level was reduced by 0.12% (v/v) at 24° C. and 0.42% (v/v) at 28° C., confirming the results obtained in synthetic must. These results highlight a more flexible metabolism in the evolved strain regarding temperature, with the reduction of ethanol yield maximized at a temperature of 28° C. and above.

TABLE 1

Metabolites, carbon and redox balances, and markers of fermentation for EC1118 and evolved strains measured after 30 days of fermentation on MS210, 260 g/L glucose, 28° C.

| Main compounds (g/L) | EC1118 | K200.1(a) | K250.1(a) | K300.2(a) | K200.1(b) | K250.3(b) | K300.1(b) |
|---|---|---|---|---|---|---|---|
| consummed glucose | 259.9 ± 0.1 | 258.5 ± 1.4 | 250.7 ± 4.5 | 251.3 ± 5.0 | 260.0 ± 0.1 | 258.6 ± 1.5 | 259.8 ± 0.3 |
| $CO_2$ | 117 ± 0 | 112 ± 1 | 110 ± 1 | 109 ± 1 | 112 ± 0 | 112 ± 2 | 110 ± 1 |
| biomass (80%)* | 4.0 ± 0.1 | 3.8 ± 0.1 | 4.0 ± 0.2 | 3.7 ± 0.2 | 3.6 ± 0.2 | 3.9 ± 0.0 | 4.0 ± 0.1 |
| ethanol | 120.6 ± 0.6 | 116.3 ± 1.3 | 112.9 ± 1.5 | 113.2 ± 1.0 | 116.3 ± 0.7 | 115.5 ± 1.6 | 114.0 ± 0.8 |
| glycerol | 8.5 ± 0.1 | 13.2 ± 0.1 | 12.7 ± 0.1 | 12.6 ± 0.2 | 13.3 ± 0.5 | 13.9 ± 0.2 | 14.2 ± 0.3 |
| succinate | 0.9 ± 0.0 | 1.5 ± 0.1 | 1.5 ± 0.1 | 1.1 ± 0.1 | 1.5 ± 0.1 | 1.5 ± 0.1 | 1.7 ± 0.1 |
| pyruvate | 0.22 ± 0.03 | 0.20 ± 0.00 | 0.20 ± 0.01 | 0.19 ± 0.00 | 0.20 ± 0.01 | 0.19 ± 0.01 | 0.19 ± 0.02 |
| acetate | 0.9 ± 0.2 | 0.7 ± 0.0 | 0.9 ± 0.0 | 1.1 ± 0.0 | 1.0 ± 0.1 | 1.0 ± 0.2 | 1.0 ± 0.1 |
| acetaldehyde | 0.011 ± 0.001 | 0.016 ± 0.001 | 0.023 ± 0.002 | 0.031 ± 0.007 | 0.025 ± 0.005 | 0.031 ± 0.010 | 0.029 ± 0.001 |
| acetoin | nd | nd | nd | nd | nd | nd | nd |
| 2,3-butanediol | 0.45 ± 0.02 | 1.00 ± 0.09 | 0.89 ± 0.30 | 1.08 ± 0.14 | 0.87 ± 0.11 | 1.10 ± 0.18 | 1.60 ± 0.06 |
| Carbon balance$^a$ (%) | 97.6 ± 0.6 | 96.9 ± 0.8 | 97.2 ± 2.5 | 97.0 ± 2.7 | 96.4 ± 0.8 | 96.7 ± 0.8 | 95.9 ± 0.5 |
| Redox balance$^b$ (%) | 97.4 ± 0.6 | 97.3 ± 0.7 | 97.5 ± 2.1 | 97.3 ± 2.1 | 96.6 ± 0.8 | 97.1 ± 1.7 | 96.4 ± 0.6 |
| YEtOH | 0.464 ± 0.002 | 0.450 ± 0.004 | 0.450 ± 0.010 | 0.450 ± 0.010 | 0.447 ± 0.003 | 0.447 ± 0.009 | 0.440 ± 0.003 |
| Yglycerol | 0.033 ± 0.000 | 0.051 ± 0.000 | 0.051 ± 0.001 | 0.050 ± 0.002 | 0.051 ± 0.002 | 0.054 ± 0.001 | 0.054 ± 0.001 |
| Yglycerol/YEtOH (%) | 7.05 ± 0.07 | 11.32 ± 0.09 | 11.27 ± 0.11 | 10.09 ± 0.23 | 11.46 ± 0.40 | 12.01 ± 0.26 | 12.38 ± 0.27 |
| ethanol** (%(v/v)) | 15.29 ± 0.08 | 14.82 ± 0.13 | 14.84 ± 0.32 | 14.84 ± 0.34 | 14.74 ± 0.09 | 14.72 ± 0.29 | 14.50 ± 0.09 |
| glucose (g) for 1%(v/v) ethanol | 17.00 ± 0.07 | 17.53 ± 0.09 | 17.52 ± 0.11 | 17.52 ± 0.23 | 17.64 ± 0.40 | 17.67 ± 0.26 | 17.97 ± 0.27 |
| residual sugar$^\$$ (g/L) | 0.1 ± 0.1 | 20.2 ± 1.4 | 58.7 ± 4.5 | 30.4 ± 5.0 | 0.1 ± 0.1 | 22.5 ± 1.5 | 0.2 ± 0.3 |
| residual sugar$^{\$\$}$ (g/L) | 0.1 ± 0.1 | 1.5 ± 1.4 | 9.3 ± 4.5 | 8.7 ± 5.0 | 0.0 ± 0.1 | 1.4 ± 1.5 | 0.1 ± 0.3 |

$^a$Carbon balance represents the ratio between carbon moles of fermentation by-products and carbon moles of glucose.
$^b$Redox balance represents the ratio between the reductance degree of fermentation by-products and the reductance degree of glucose. Both balances are expressed in percentage.
nd: not detected (<10 mg/L)
*Biomass measured at 80% of fermentation advancement
**Potential ethanol
$^\$$Measured after 15 days
$^{\$\$}$Measured after 30 days Pilot-Scale Assessment of the Evolved Strain K300.1(b).

To validate the results obtained at laboratory scale, the behavior and the metabolic properties of K300.1(b) and EC1118 were compared during pilot scale fermentation, using a Grenache grape must, at 28° C. (Table 2).

TABLE 2

Characteristics of wines obtained by fermentation of Grenache must with EC1118 and K300.1(b) at pilot scale (1 hL). ASV was determined by distillation and electronic densitometry.

|  | EC1118 | K300.1(b) |
| --- | --- | --- |
| residual sugars (g/L) | 0.2 | 0.5 |
| volatil acidity (g/L) | 0.50 | 0.36 |
| total acidity (g/L) | 4.10 | 4.40 |
| ASV % v/v) | 16.26 | 15.80 |
| pH | 3.60 | 3.57 |
| free $SO_2$ (g/L) | 0.07 | 0.07 |
| total $SO_2$ (g/L) | 0.035 | 0.039 |
| acetaldehyde (g/L) | 0.021 | 0.030 |
| malate (g/L) | 1.35 | 1.38 |
| succinate (g/L) | 1.04 | 1.43 |
| acetate (g/L) | 0.47 | 0.31 |
| glycerol (g/L) | 10.8 | 14.2 |

Figure 5:
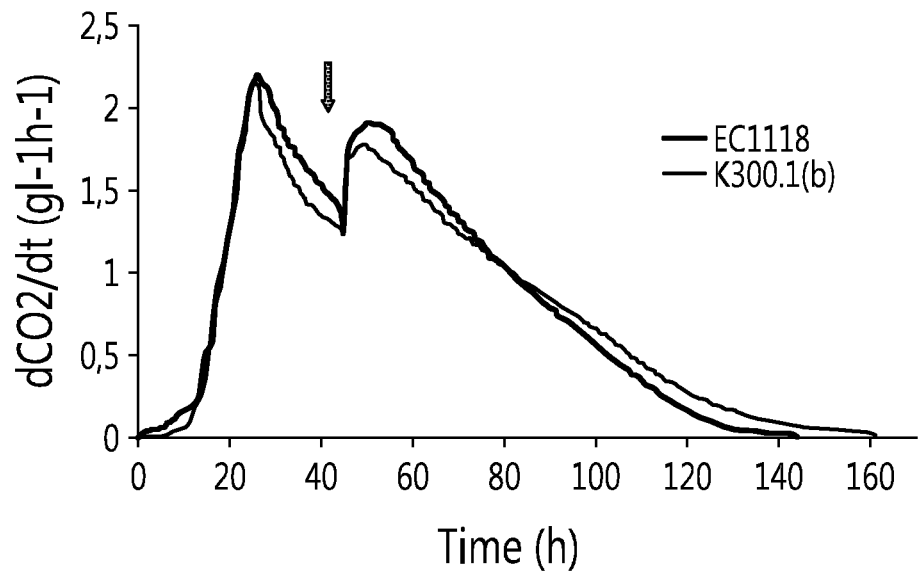
FIG. 5 illustrates the kinetics of wine fermentation on Grenache for EC1118 (black line) and K300.1(b) (dark grey line). 72 mg/L nitrogen (15 g/hL of DAP and 30 g/hL of Fermaid®E) were added at the time point indicated by an arrow. Results are shown as $dCO_2/dt(g/L/H)$ in function of time (hours). Each points includes the measured valued as well as the standard deviation.

To be as close as possible to industrial conditions, the strains K300.1(b) and EC1118 were used in the form of active dry yeast and inoculated after a standard rehydration procedure. To avoid stuck fermentation, oxygen and nitrogen were added during fermentation (FIG. 5). The evolved strain had a fermentation rate slightly lower than EC1118, but was able to complete the fermentation, despite the high sugar concentration (270 g/L). The evolved strain produced more glycerol (14.2 g/L versus 10.8 g/L) and succinate than EC1118, and less ethanol, resulting in a reduction of 0.46% (v/v) of the ethanol content. These results are in agreement with those obtained at laboratory scale. The production of acetic acid and volatile acidity by the evolved strain was clearly lower than for EC1118. The production of acetic acid for both strains was much lower than on synthetic must, which is in agreement with previous observations. In summary, the results obtained in grape must at pilot-scale confirm the metabolic reprogramming of the evolved strain, and the analysis of the wine obtained did not reveal adverse side effects.

In this study, adaptive laboratory evolution (ALE) was used to develop low-alcohol wine yeasts by redirecting the metabolism of strain EC1118 towards glycerol. Yeast cultures were serially transferred in hyperosmotic conditions during 450 generations using KCl as osmo- and salt-stress salt. The stress imposed was severe, from osmolalities of 2 105 to 3 730 mmol/kg. These levels of stress are above those generally used in laboratory conditions to study responses to osmotic stress (20 g/L glucose, 1.2 M NaCl, corresponding to an osmolality of 2 070 mmol/kg). The KCl stress generated strains in which the carbon flux was re-directed towards glycerol. In another experiment, sorbitol was used as an osmotic salt (from 1.5 to 2.4 g/L corresponding to 1 480 to 2 105 mmol/kg), but these conditions failed to generate strains with increased glycerol production (data not shown). This clear difference in effect may be a consequence of the different natures of the stress salt (salt versus osmotic stress), and/or the higher level of stress in the KCl-ALE experiment than the sorbitol-ALE experiment. The evolved strains obtained from the KCl-ALE experiment were not more resistant than the ancestral strain to osmotic or salt stress, but showed a gain of fitness due to a better viability under conditions of salt stress and carbon starvation, the conditions in which cells were transferred to a fresh medium. No increase in glycerol production was observed in the ALE control experiment with EC1118 without KCl stress (data not shown). Therefore, it is likely that the redirection of carbon fluxes towards glycerol was driven by the combination of high KCl concentration and carbon starvation stresses.

The link between survival and glycerol is intriguing. Usually, cells die after the culture enters the stationary phase, when one or all of the nutrients are missing. However, if the only nutrient missing is the carbon source, cells survive longer. Without wishing to be bound to theory, it is stipulated that, under carbon limitation, nutrient sensing depends on Sch9, Tor, and Ras proteins that are activated and converge on the protein kinase Rim15; Rim15 regulates the transcription factors Msn4/Msn2 and Gis1, involved in cellular protection and longevity, also called chronological life span (CLS). Recent work indicates that glycerol production is required for CLS regulation), and various distinct mechanisms have been suggested. Unlike glucose and ethanol, glycerol does not inhibit the transactivation of Msn2/Msn4 and Gis1, which play important roles in general stress resistance and longevity. However, glycerol production may affect aging through the modulation of the intracellular redox balance, because its production contributes to the maintenance of the $NAD^+/NADH$ ratio. Overexpression of the malate-aspartate NADH shuttle was also demonstrated to extend the CLS. Also, high osmolarity has been postulated to extend the life span by activating Hog1, leading to an increase in the biosynthesis of glycerol from glycolytic intermediates. Links between aging and redox metabolism during wine fermentation have also been highlighted.

The detailed characterization of the KCl-evolved mutants during wine fermentation revealed that the evolved strains had undergone substantial changes to their central carbon metabolism: carbons in these strains are mainly re-routed towards glycerol, succinate and 2,3-butanediol at the expense of ethanol. The absence of stress resistance phenotype and the improved fitness under carbon restricted and stress conditions suggest that the primary target of evolution is not the HOG pathway. The origin of the observed phenotype might rely on indirect mutations disturbing the redox balance, causing a redirection of carbon flux. Other factors such as a lower glucose uptake rate might also play a role in the phenotype. Indeed, the net flux through the TCA cycle increased significantly with decreasing glucose uptake, which is reminiscent of the increased succinate production and lower fermentation rate in the evolved strains. On the other hand, it was previously shown that glycerol production is less dependent on rate of glucose uptake and more influenced by environmental conditions. Other studies using genome-wide approaches may be required to elucidate the underlying mechanisms.

As observed previously in engineered strains overexpressing GPD1 (Michnick et al., Remize et al., Cambon et al.), increased glycerol production is associated with a reduction of ethanol synthesis due to lower carbon availability and NADH shortage, and this is accompanied by perturbations at the acetaldehyde and pyruvate nodes. For example, strains overexpressing GPD1, and producing large amounts of glycerol but low ethanol levels, accumulate succinate and 2,3-butanediol but also undesirable compounds including acetaldehyde, acetate and acetoin (Remize et al., Cambon et al.). The evolved strain described herein did not accumulate high levels of these compounds, possibly due, for example, to the smaller increase in glycerol production than in the engineered strains, and/or to a different metabolic strategy. In yeast, acetoin is reduced to 2,3-butanediol by the 2,3-butanediol dehydrogenase. It was previously showed that the balance between acetoin and 2,3-butanediol in the engineered strains can be influenced by the amounts of glycerol produced. In strains producing high glycerol levels, acetoin accumulated because of the limited capacity of the 2,3 butanediol dehydrogenase and the decreased availability of NADH, as this cofactor is mainlyre-oxidized through glycerol synthesis. In a previous study (Michnick et al.), it was found that strains overproducing glycerol at moderate levels (such as W18GPD1 or W6GPD1), comparable to the evolved mutants characterized herein, did not accumulate acetoin. As the evolved strains, these strains also accumulated acetaldehyde at low levels, which can be explained by a limitation of the alcohol dehydrogenase. These levels remain in the range of usual concentrations in wines and are unlikely to cause a sensory problem. In contrast, the reduced accumulation of acetate by the evolved mutants is surprising because there was acetate accumulation in all cases, independent of the level of glycerol accumulated by the GPD1 strains (Blomberg et al.). This suggests that the modifications of the metabolic network in the evolved mutants differ from those in the genetically engineered strains. Without wishing to be bound to theory, another major difference involves the compromised fermentation performances of the evolved strains, suggesting that the mutations responsible for the re-routing of metabolism in these strains also negatively affect the glycolytic rate. This finding contrasts with the improved fermentation performances of GPD1 strains during the stationary phase of wine fermentation.

It is thus hypothesized that adaptive evolution resulted in the utilization of routes different to those operating in rationally engineered strains. The present disclosure provides the first description of a non-GMO strategy allowing a substantial increase in glycerol production and decrease in the alcohol yield of a commercial wine yeast strain. A much higher diversion of carbon was obtained when compare to previous attempts to divert carbons towards the pentose phosphate pathway or towards glycerol by adaptive evolution using sulfites (Kutyna et al.). Consequently, the reduction in the ethanol content of wine produced with our strains was at least 0.5% (v/v) from 260 g/L sugars. Despite the lower fermentation performances of the evolved strains, evolved isolates with only slightly affected fermentation kinetics were selected. A first assessment of the potential value of the evolved strain K300.1(b) for winemaking revealed similar characteristics in synthetic and natural grape musts, except that acetate production was reduced in wines obtained from grape musts. Interestingly, evolved strain K300.1(b) has a higher metabolic flexibility than the ancestral strain with respect to temperature, with metabolic differences between the two strains being greatest at temperatures higher than 24° C. This suggests that the evolved strain might be particularly useful for the production of red wines, which are usually produced in a temperature range of 25-30° C. and are most affected by excessive alcohol levels.

The present example demonstrates that the adaptive evolution strategy used herein is a valuable alternative to rational engineering for the generation of non-GMO, low-ethanol producing yeast. Although the diversion of carbon flux obtained is not as high as that achieved by genetic engineering, a reduction of the alcohol content of wine by 0.5 to 1% (v/v) offers interesting perspectives. A preliminary wine tasting by a panel of seven wine experts did not revealed any defect of the wines produced at pilot scale, confirming the good overall attributes of the evolved strains reported in this study.

Example II

Second Generation of Low-Ethanol Producing Yeasts Obtained by Breeding

The *S. cerevisiae* strain K300.1(b) (obtained and characterized in Example I and renamed Lowa3 in Example II) was cultured (2 days at 28° C.) in a presporulation GNA medium (BactoYeast extract 1%, BactoPeptone 2%, glucose 20%, agar 2%). The Lowa3 strain was then transferred in a sporulation spoMA medium (BactoYeastExtract 0.1%, glucose 0.05%, potassium acetate 1%, adenine 0.002%) and cultured between 3 to 15 days at room temperature (about 20° C.) to produce asci. The asci obtained were isolated and incubated with the digestive juice of the snail *Helix pomatia* (1/6 dilution) for 20 to 60 min at 28° C. The asci were dissected with a dissection microscope (Singer MSM300) to isolate the spores. With this method, about 700 spores were isolated.

Since the *S. cerevisiae* strain EC1118 and the Lowa3 strain are heterozygotes for the HO gene, it is expected that half of the progeny will be haploid, whereas the other half of the progeny will be diploid. As such, a PCR selection was undertaken to select the haploid progeny (e.g., $HO^{-/-}$) of the Lowa3 strain. The PCR was performed on a part of a colony the diluted in 50 μL of sterile water and heated for 10 min at 95° C. to liberate the DNA. Five (5) μL of the aqueous DNA mixture was admixed to 10× Taq buffer (with $(NH_4)_2SO_4$; 2.5 μL), 25 mM $MgCl_2$ (2.5 μL), 10 mM dNTPs (0.5 μL), the MAT-F primer (1 μL), the MATa-R or MATalpha-R primer (1 μL), Taq polymerase (Fermentas, 0.25 μL) and water to obtain a final volume of 25 μL. The following oligonucleotides were used to distinguish between the MATa and MATalpha genes: Mat F (5'-AGTCACAT-CAAGATCGTTTATGG-3') (SEQ ID NO: 1), Mat a-R (5'-ACTCCACTTCAAGTAAGAGTTTG-3', generating a 504 bp amplicon of the MATa gene) (SEQ ID NO: 2) and Mat alpha-R (5'-GCACGGAATATGGGACTACTTCG-3', generating a 404 bp amplicon of the MATalpha gene) (SEQ ID NO: 3). The PCR was conducted during 30 cycles using a denaturation temperature of 94° C. (for 1 min), an hybridization temperature of 55° C. (for 1 min) and an elongation temperature of 72° C. (for 1 min).

Using the PCR selection, 156 haploid spores of the Lowa3 strain were obtained. The phenotype of the haploid spores was further characterized during wine fermentation. Several wine fermentations were conducted in 330 mL fermenters containing 300 mL synthetic must (MS425, 260 g/L glucose) under agitation. After 15 and 30 days of fermentation at 28° C., a sample of the supernatant was obtained to determine the glycerol concentration. The different haploid strains were classified in function of their glycerol production (which is inversely proportional to their ethanol production). The best strain of the MATa mating type, named 5074, produced 20.9 g/L glycerol. The best strain of the MATalpha mating type, named 5049, produced 16.2 g/L glycerol. Strains 5074 and 5049 were selected for further breeding.

Both strains were cultured to be in their growth phase and were contacted in a YPD medium (BactoYeast extract 1%, BactoPeptone 2%, glucose 2%, agar 2%). A first hybrid was obtained, named VT1 (H1 generation hybrid). The diploid nature of the VT1 hybrid was confirmed by the absence of breeding when it was placed in contact with a strain of the MATa mating type and with a strain of the MATalpha mating type.

Spores of the hybrid strain VT1 were generated with the medium GNA and spoMA as described above. A stable haploid spore of the hybrid VT1 strain, named MP120-A4 was selected based on its MATalpha mating type. The strain MP120-A4 was bred with the strain 5074 to obtain the strain MP112-A5 (H2 generation hybrid). Strain MP112-A5 (also referred as H2) was registered under CNCM I-4832 as a biological deposit in the Collection National de Cultures de Microorganismes (CNCM) of the Institut Pasteur on Jan. 9, 2014.

The various strains obtained were further characterized using a laboratory scale or pilot scale wine fermentation, as described in Example I, and following the kinetics of each fermentations.

Fermentation Trial N1.

A synthetic must was used and has an initial concentration in sugar of 235 g/L (117.5 g/L of glucose and 117.5 g/L of fructose). The initial concentration in available nitrogen in this synthetic must was 300 mg/L. All the fermentations were conducted in isotherm conditions at 28° C., in 1.1 L-containing fermenters.

Figure 6:
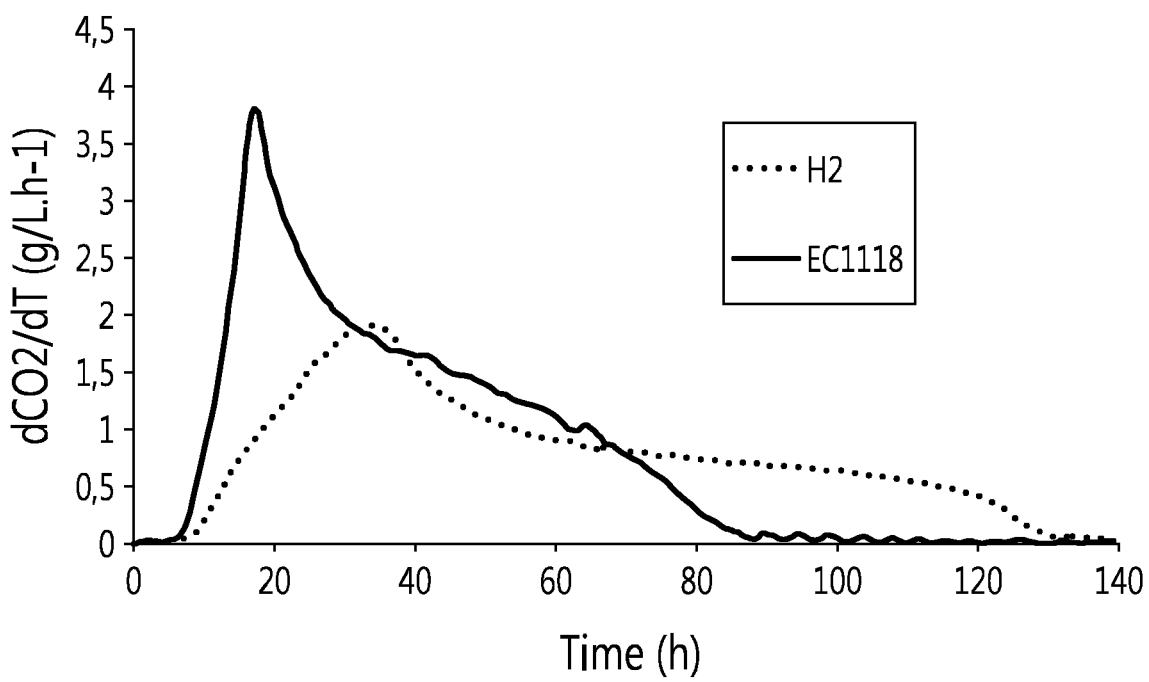
FIG. 6 illustrates the kinetics of wine fermentation trial N2 on synthetic must containing 235 g/L sugars for the ancestral strain (EC1118) and an H2 generation hybrid. Results are shown as $dCO_2/dt(g/L/H)$ in function of time (hours).

As shown on FIG. 6, 112-A5 (H2) was compared with EC1118 to ferment the same must with a 14% v/v potential alcohol. As previously described, the fermentation kinetic profiles are very different on the exponential phase with a better fermentation rate of EC1118. The evolved yeast strain (112-A5) had a long stationary phase and completed the fermentation much later than EC1118. However, the fermentation went to dryness, meaning there is no residual sugars. This is confirmed by the analysis in Table 4. The use of 112-A5 allowed to ferment with a significant lower final ethanol level. Another difference is observed on the final acetate content which is significantly lower with 112-A5. Further differences between the fermentations obtained using the EC1118 or the 112-A5 strains are presented at Table 4.

TABLE 4

Analysis of various constituents of the fermented wine obtained at fermentation trial N1 using the EC1118 or the 112-A5 strains. The glycerol content was not determined.

|  | Sugar/Ethanol yield | ASV (% v/v) | Acetate content (g/L) | Residual sugars (g/L) |
| --- | --- | --- | --- | --- |
| EC1118 | 16.67 | 14.09 | 0.66 | <0.4 |
| 112-A5 | 17.5 | 13.45 | 0.5 | <0.4 |

Fermentation Trial N2.

A synthetic must was used and has an initial concentration in sugar of 260 g/L (130 g/L of glucose and 130 g/L of fructose). The initial concentration in available nitrogen in this synthetic must was 300 mg/L. All the fermentations were conducted in isotherm conditions at 28° C., in 1.1 L-containing fermenters.

Figure 7:
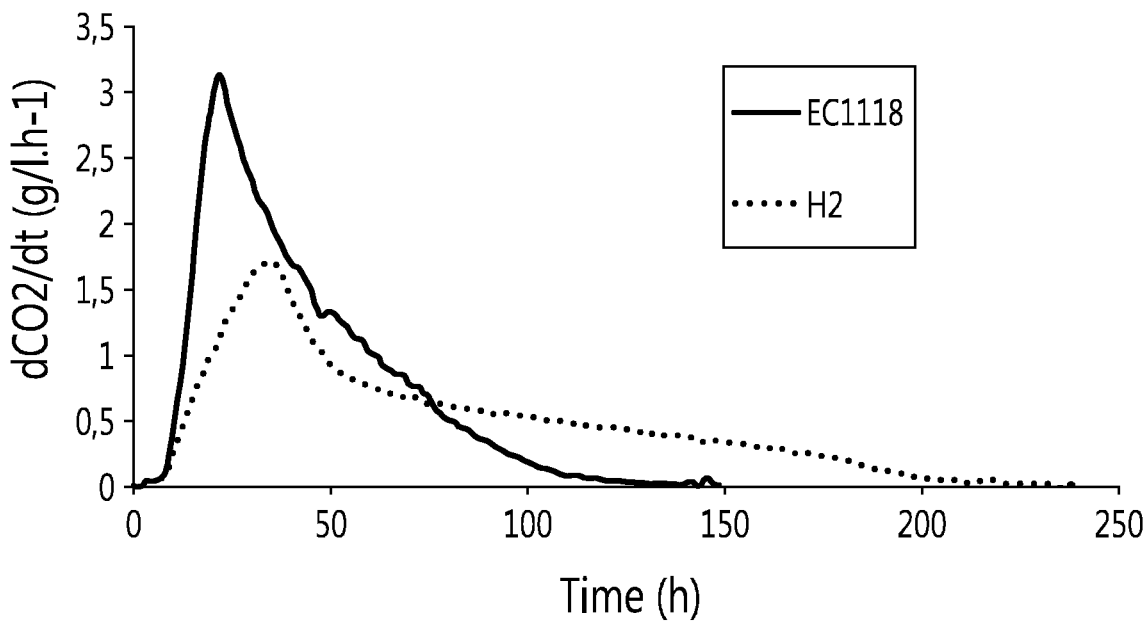
FIG. 7 illustrates the kinetics of wine fermentation trial N3 on synthetic must containing 260 g/L sugars for the ancestral strain (EC1118) and an H2 generation hybrid. Results are shown as $dCO_2/dt(g/L/H)$ in function of time (hours).

As shown on FIG. 7, 112-A5 (H2) was compared with EC1118 to ferment the same must with a 15.6% v/v potential alcohol. As previously described, the fermentation kinetic profiles are very different on the exponential phase with a better fermentation rate of EC1118. The evolved yeast strain (112-A5) had a long stationary phase and completed the fermentation much later than EC1118. However, the fermentation went to dryness, meaning there is no residual sugars. This is confirmed by the analysis in Table 5. The use of 112-A5 allowed to ferment with a significant lower final ethanol level. Another difference is observed on the final acetate content which is significantly lower with 112-A5. Further differences between the fermentations using the EC1118 or the 112-A5 strains are presented at Table 5.

TABLE 5

Analysis of various constituents of the fermented wine obtained in fermentation trial N2 using the EC1118 or the 112-A5 strains. The glycerol content was not determined.

|  | Sugar/Ethanol yield | ASV (% v/v) | Acetate content (g/L) | Residual sugars (g/L) |
| --- | --- | --- | --- | --- |
| EC1118 | 16.7 | 15.56 | 0.68 | 0.4 |
| H2 | 17.6 | 14.75 | 0.51 | 1.0 |

Fermentation Trial N3.

A Syrah variety grape must was used in this pilot scale fermentation trial. The must was flash pasteurized and stored at 2° C. prior to fermentation. Prior to fermentation, the Syrah must had the following characteristics: 255 g/L of total sugars, 3.50 g/L $H_2SO_4$ of total acidity, pH=3.63, 138 mg/L of available nitrogen and a turbidity of 77 NTU. Prior to fermentation, and as indicated in Example I, the yeasts were rehydrated. Further, during fermentation, the must was supplemented with oxygen and nitrogen (as indicated in Example I). All the fermentations were conducted in isotherm conditions at 28° C., in 1 hL-containing fermenters. Afterwards, the wines were bottled.

Figure 8:
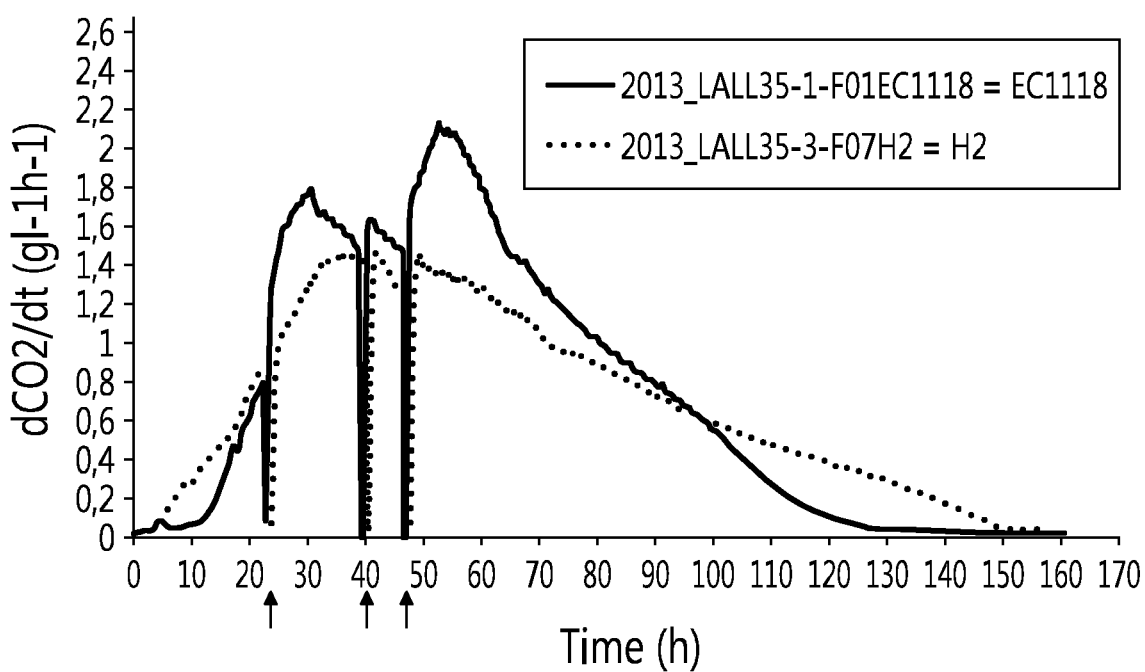
FIG. 8 illustrates the kinetics of wine fermentation trial N4 on a Syrah variety grape must for the ancestral strain (EC1118) and an H2 generation hybrid (120-A5). Results are shown as $dCO_2/dt(g/L/H)$ in function of time (hours). Arrows indicated when oxygen was added to the fermentation.

FIG. 8 shows the fermentative kinetics of EC1118, K300.1(b) (Lowa3) and 112-A5 (H2) in real grapes, in enological conditions. The profiles are different but the performances on the total fermentation duration quite similar, showing a delay of only 20 h for the fermentation with 112-A5. This confirms that 112-A5 is suitable to ferment high sugar grapes till dryness, without stuck or sluggish fermentations. This is confirmed by the analysis of the classical enological parameters reported in table 6A and 6B. The final ethanol level shows a decrease of more than 1% for the wine fermented with 112-A5, with a higher glycerol production and a very low acetate production (not detected). Further differences between the fermentations using the EC1118 or the 112-A5 strains are presented at Tables 6.

TABLE 6A

Kinetics parameters of the wine fermentation using the EC1118 or the 112-A5 strains in fermentation trial N3.

|  | Latency period (h) | Vmax (g/L/h) after addition | Residual sugars (g/L) | Time of fermentation trial (h) |
| --- | --- | --- | --- | --- |
| EC1118 | 11 | 2.13 | 0.3 | 130 |
| 112-A5 | 1 | 1.47 | 0.4 | 150 |

TABLES 6B

Analysis of various constituents of the fermented wine obtained in fermentation trial N3 using the EC1118, the K300.1(b) or the 112-A5 (H2) strains. Measurements were done in triplicates.

|  | EC1118 | K300.1(b) | H2 |
| --- | --- | --- | --- |
| Main compounds (g/L) |  |  |  |
| consumed sugar | 254.6 ± 0.1 | 254.5 ± 0.0 | 254.7 ± 0.2 |
| ethanol | 118.4 ± 1.2 | 113.6 ± 0.9 | 107.8 ± 0.8 |

TABLES 6B-continued

Analysis of various constituents of the fermented wine obtained in fermentation trial N3 using the EC1118, the K300.1(b) or the 112-A5 (H2) strains. Measurements were done in triplicates.

|  | EC1118 | K300.1(b) | H2 |
|---|---|---|---|
| glycerol | 10.8 ± 0.4 | 14.1 ± 0.4 | 17.9 ± 0.8 |
| succinate | 1.3 ± 0.1 | 1.8 ± 0.1 | 1.5 ± 0.1 |
| pyruvate | 0.13 ± 0.01 | 0.16 ± 0.01 | 0.15 ± 0.01 |
| acetate | 0.5 ± 0.1 | 0.1 ± 0.0 | nd |
| acetaldehyde | 0.016 ± 0.008 | 0.021 ± 0.001 | 0.020 ± 0.006 |
| acetoin | nd | nd | 0.024 ± 0.005 |
| 2,3-butanediol | 1.11 ± 0.18 | 1.98 ± 0.38 | 3.93 ± 0.30 |
| YEtOH | 0.465 ± 0.005 | 0.446 ± 0.003 | 0.423 ± 0.003 |
| Yglycerol | 0.042 ± 0.002 | 0.055 ± 0.000 | 0.070 ± 0.003 |
| Yglycerol/YEtOH (%) | 9.09 ± 0.34 | 12.37 ± 0.05 | 16.57 ± 0.84 |
| ethanol (%(v/v)) | 15.01 ± 0.15 | 14.40 ± 0.11 | 13.67 ± 0.10 |
| glucose (g) for 1% (v/v) ethanol | 16.99 ± 0.07 | 17.71 ± 0.07 | 18.66 ± 0.08 | nd: not detected (<10 mg/mL)

While the invention has been described in connection with specific embodiments thereof, it will be understood that the scope of the claims should not be limited by the preferred embodiments set forth in the examples, but should be given the broadest interpretation consistent with the description as a whole.

REFERENCES

Aguera E, Sablayrolles J M. Pilot scale vinifications (100 L). III Controlled fermentation. Wine Internet Tech. J. 8.

Bely M, Sablayrolles J M, Barre P. 1990. Automatic detection of assimilable nitrogen deficiencies during alcoholic fermentation in oenological conditions. J. Ferment. Bioeng. 70:246-252.

Blomberg A, Adler L. 1992. Physiology of osmotolerance in fungi. Adv. Microb. Physiol. 33:145-212.

Cambon B, Monteil V, Remize F, Camarasa C, Dequin S. 2006. Effects of GPD1 overexpression in *Saccharomyces cerevisiae* commercial wine yeast strains lacking ALD6 genes. Appl. Environ. Microbiol. 72:4688-4694.

Hagenauer-Hener U, Henn D, Fettmar F, Mosandl A, Schmitt A. 1990. 2,3 Butanediol-Direkte Bestimmung der Stereoisomeren im Wein. Dtsch Leb. Rundsch 273-276.

Kutyna D R, Varela C, Stanley G A, Borneman A R, Henschke P A, Chambers P J. 2012. Adaptive evolution of *Saccharomyces cerevisiae* to generate strains with enhanced glycerol production. Appl. Microbiol. Biotechnol. 93:1175-1184.

Lundquist F. Acetaldehyd: Bestimmung mit Aldehyd-dehydrogenase. Methods of enzymatic analysis. Methods Enzym. Anal.

Michnick S, Roustan J L, Remize F, Barre P, Dequin S. 1997. Modulation of glycerol and ethanol yields during alcoholic fermentation in *Saccharomyces cerevisiae* strains overexpressed or disrupted for GPD1 encoding glycerol 3-phosphate dehydrogenase. Yeast Chichester Engl. 13:783-793.

Remize F, Roustan J L, Sablayrolles J M, Barre P, Dequin D. 1999. Glycerol overproduction by engineered *Saccharomyces cerevisiae* wine yeast strains leads to substantial changes in By-product formation and to a stimulation of fermentation rate in stationary phase. Appl. Environ. Microbiol. 65:143-149.

What is claimed is:

1. A variant yeast strain capable of producing, when compared to an ancestral yeast strain, more glycerol and less ethanol and less acetate in an alcoholic fermentation process, said variant yeast being obtained by a process comprising:
   a) culturing the ancestral yeast strain in a first culture medium comprising a salt capable of causing hyperosmotic stress to the ancestral yeast strain, wherein the ancestral yeast strain is cultured in increasing salt concentrations and under conditions to achieve glucose depletion in the first culture medium so as to obtain a first cultured yeast strain; and
   b) culturing the first cultured yeast strain in a second culture medium comprising the salt that is capable of causing hyperosmotic stress to the ancestral yeast strain, wherein the first cultured yeast strain is cultured at a fixed salt concentration and under conditions to achieve glucose depletion in the second culture medium so as to obtain the variant yeast strain; wherein:
      i. the salt has a counter-cation which is different than a sodium cation; and
      ii. the concentration of the salt in the second culture medium is higher than the concentration of the salt in the first culture medium,
   wherein the ancestral yeast strain and the variant yeast strain are non-genetically modified yeast strains.

2. The variant yeast strain of claim 1 which is capable of making a fermented product when contacted with a fermentable source of nutrients, wherein the fermentable source of nutrients is a grape must and the fermented product is wine.

3. The variant yeast strain of claim 2 wherein the wine is red wine.

4. A variant yeast strain deposited at Institut Pasteur, on Jan. 9, 2014, under accession number Collection Nationale des Cultures des Microorganismes (CNCM) I-4832.

5. A variant yeast strain deposited at Institut Pasteur, on Oct. 18, 2012 under accession number Collection Nationale des Cultures des Microorganismes (CNCM) I-4684.

6. A variant yeast strain deposited at Institut Pasteur, on Jan. 28, 2015 under accession number Collection Nationale des Cultures des Microorganismes (CNCM) I-4952.

7. A process for obtaining a variant yeast strain of claim 1 capable of producing, when compared to an ancestral yeast strain, more glycerol and less ethanol and less acetate during an alcoholic fermentation process, said process comprising:
   a) culturing the ancestral yeast strain in a first culture medium comprising a salt capable of causing hyperosmotic stress to the ancestral yeast strain, wherein the ancestral yeast strain is cultured in increasing salt concentrations and under conditions to achieve glucose depletion in the first culture medium so as to obtain a first cultured yeast strain; and
   b) culturing the first cultured yeast strain in a second culture medium comprising the salt that is capable of causing hyperosmotic stress to the ancestral yeast strain, wherein the first cultured yeast strain is cultured at a fixed salt concentration and under conditions to achieve glucose depletion in the second culture medium so as to obtain the variant yeast strain;
   wherein
      the salt has a countercation which is different than a sodium cation; and
      the concentration of the salt in the second culture medium is higher than the concentration of the salt in the first culture medium, wherein the ancestral yeast strain and the variant yeast strain are non-genetically modified yeast strains.

8. The process of claim 7, wherein either or both of (i) concentration of the salt in the first culture medium is between about 1.25 M and less than about 2.4 M and (ii) concentration of the salt in the second culture medium is at least about 2.4 M.

9. The process of claim 7, further comprising, at step a), increasing the salt concentration weekly or increasing the salt concentration monthly.

10. The process of claim 7, wherein the first culture medium comprises glucose and the process further comprises, at step a), culturing the ancestral yeast strain in the first culture medium in which glucose concentration is decreased weekly or in which glucose concentration is decreased monthly, wherein the glucose concentration in the first culture medium is between about 14.0% and about 8.0% (w/v) with respect to total volume of the first culture medium.

11. The process of claim 7, wherein the second culture medium comprises glucose and the process further comprises, at step b), culturing the first cultured yeast strain at a fixed glucose concentration wherein the fixed glucose concentration of the second culture medium is about 8.0% (w/v) with respect to total volume of the second culture medium.

12. The process of claim 7, further comprising mating haploid spores of the variant yeast strain to obtain a variant hybrid strain.

13. The process of claim 7, wherein the salt has a potassium countercation.

14. The process of claim 13, wherein the salt is KCl.

15. The process of claim 7, wherein the variant yeast strain is obtained from a *Saccharomyces* species.

16. The process of claim 15, wherein the *Saccharomyces* species is selected from the group consisting of *Saccharomyces arboricolus, Saccharomyces eubayanus, Saccharomyces bayanus, Saccharomyces cerevisiae, Saccharomyces kudriavzevii, Saccharomyces mikatae, Saccharomyces paradoxus, Saccharomyces pastorianus, Saccharomyces carlsbergensis, Saccharomyces uvarum* and inter-species hybrids thereof.

17. A process for making a fermented product, said process comprising contacting the variant yeast strain of claim 1 with a fermentable source of nutrients.

18. The process of claim 17, wherein the fermented product is wine and the fermentable source of nutrients is a grape must.

19. The process of claim 18 wherein the wine is red wine.

\* \* \* \* \*